United States Patent [19]

Clitherow et al.

[11] Patent Number: 5,340,810

[45] Date of Patent: Aug. 23, 1994

[54] BENZANILIDE DERIVATIVES

[75] Inventors: John W. Clitherow; Malcolm Carter, all of Ware, Great Britain

[73] Assignee: Glaxo Group Limited, London, England

[21] Appl. No.: 946,098

[22] Filed: Sep. 17, 1992

[30] Foreign Application Priority Data

Sep. 18, 1991 [GB] United Kingdom ............... 9119931
Mar. 12, 1992 [GB] United Kingdom ............... 9205338

[51] Int. Cl.⁵ ............... A61K 31/495; C07D 403/12; C07D 413/12
[52] U.S. Cl. ............... 514/252; 544/366; 544/367; 544/229; 544/385; 544/393; 544/395; 548/110; 548/128; 548/131; 548/133; 548/127; 548/143; 548/136; 548/269.4; 560/103; 564/149; 564/253; 564/442
[58] Field of Search ............... 544/366, 367; 514/252

[56] References Cited

U.S. PATENT DOCUMENTS

| | | | |
|---|---|---|---|
| 3,192,213 | 6/1965 | Krapcho | 564/182 |
| 4,058,523 | 11/1977 | Mori et al. | 544/165 |
| 4,123,432 | 10/1978 | Sellstedt et al. | 544/366 |
| 4,353,904 | 10/1982 | Thieme et al. | 514/252 |
| 4,735,959 | 4/1988 | Grell et al. | 514/357 |

FOREIGN PATENT DOCUMENTS

| | | |
|---|---|---|
| 85/43116 | 12/1985 | Australia . |
| 86/67002 | 7/1987 | Australia . |
| 0034276 | 8/1981 | European Pat. Off. . |
| 0058779 | 9/1982 | European Pat. Off. . |
| 0210782 | 2/1987 | European Pat. Off. . |
| 0253310 | 1/1988 | European Pat. Off. . |
| 0288189 | 10/1988 | European Pat. Off. . |
| 0310370 | 4/1989 | European Pat. Off. . |
| 0324521 | 7/1989 | European Pat. Off. . |
| 0335381 | 10/1989 | European Pat. Off. . |
| 0365064 | 4/1990 | European Pat. Off. . |
| 2545978 | 4/1976 | Fed. Rep. of Germany . |
| 1157586 | 7/1969 | United Kingdom . |
| 84/00545 | 2/1984 | World Int. Prop. O. . |

OTHER PUBLICATIONS

Charles et al., *Archiv der Pharmazie*, vol. 315, No. 2, pp. 97–103 (Feb. 1982).

*Primary Examiner*—Emily Bernhardt
*Attorney, Agent, or Firm*—Bacon & Thomas

[57] ABSTRACT

The invention provides compounds of formula (I):

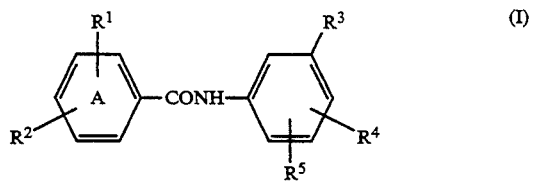

or a physiologically acceptable salt or solvate thereof wherein $R^1$ represents a hydrogen atom or a halogen atom or a group selected from $C_{1-6}$alkyl and $C_{1-6}$alkoxy;

$R^2$ represents a phenyl group substituted by a group selected from

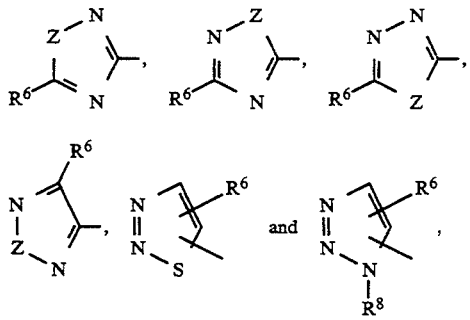

and optionally further substituted by one or two substituents selected from halogen atoms, $C_{1-6}$alkoxy, hydroxy, and $C_{1-6}$alkyl;

$R^3$ represents the group (Abstract continued on next page.)

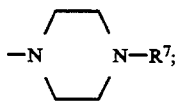

$R^4$ and $R^5$, which may be the same or different each independently represent a hydrogen atom or a halogen atom or a group selected from hydroxy, $C_{1-6}$alkoxy and $C_{1-6}$alkyl;

$R^6$ represents a hydrogen atom or a group selected from $-NR^9R^{10}$ and a $C_{1-6}$alkyl group optionally substituted by one or two substituents selected from $C_{1-6}$alkoxy, hydroxy, $C_{1-6}$acyloxy and $-SO_2R^{11}$;

$R^7$, $R^8$ and $R^9$, which may be the same or different each independently represent a hydrogen atom or a $C_{1-6}$alkyl group;

$R^{10}$ represents a hydrogen atom or a group selected from $C_{1-6}$alkyl, $C_{1-6}$acyl, benzoyl and $-SO_2R^{11}$;

$R^{11}$ represents a $C_{1-6}$alkyl group or a phenyl group;

Z represents an oxygen atom or a group selected from $NR^8$ and $S(O)_k$; and k represents zero, 1 or 2.

The compounds may be used in the treatment or prophylaxis of depression and other CNS disorders.

22 Claims, No Drawings

BENZANILIDE DERIVATIVES

This invention relates to novel benzanilide derivatives, to processes for their preparation, and to pharmaceutical compositions containing them.

According to the invention we provide compounds of the general formula (I):

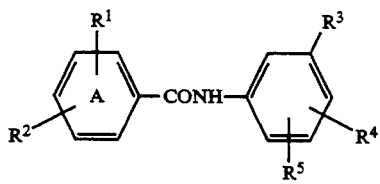

or a physiologically acceptable salt or solvate (e.g. hydrate) thereof, in which $R^1$ represents a hydrogen atom or a halogen atom or a group selected from $C_{1-6}$alkyl and $C_{1-6}$alkoxy;

$R^2$ represents a phenyl group substituted by a group selected from

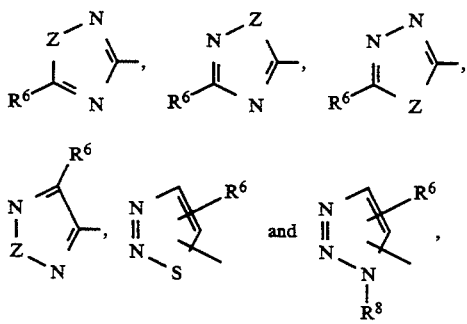

and optionally further substituted by one or two substituents selected from halogen atoms, $C_{1-6}$alkoxy, hydroxy, and $C_{1-6}$alkyl;

$R^3$ represents the group

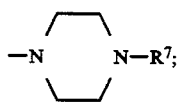

$R^4$ and $R^5$, which may be the same or different, each independently 0 represent a hydrogen atom or a halogen atom or a group selected from hydroxy, $C_{1-6}$alkoxy and $C_{1-6}$alkyl;

$R^6$ represents a hydrogen atom or a group selected from $-NR^9R^{10}$ and a $C_{1-6}$alkyl group optionally substituted by one or two substituents selected from $C_{1-6}$alkoxy hydroxy, $C_{1-6}$acyloxy and $-SO_2R^{11}$;

$R^7$, $R^8$ and $R^9$, which may be the same or different, each independently represent a hydrogen atom or a $C_{1-6}$alkyl group;

$R^{10}$ represents a hydrogen atom or a group selected from $C_{1-6}$alkyl, $C_{1-6}$acyl, benzoyl and $-SO_2R^{11}$;

$R^{11}$ represents a $C_{1-6}$alkyl group or a phenyl group;

Z represents an oxygen atom or a group selected from $NR^8$ and $S(O)_k$; and k represents zero, 1 or 2.

It is to be understood that the present invention encompasses all geometric and optical isomers of the compounds of general formula (I) and their mixtures including the racemic mixtures thereof.

Physiologically acceptable salts of the compounds of general formula (I) include acid addition salts formed with inorganic or organic acids (for example hydrochlorides, hydrobromides, sulphates, phosphates, benzoates, naphthoates, hydroxynaphthoates, p-toluenesulphonates, methanesulphonates, sulphamates, ascorbates, tartrates, citrates, oxalates, maleares, salicylates, fumarates, succinates, lactates, glutarates, glutaconates, acetates or tricarballylates).

In the compounds of general formula (I), the term '$C_{1-6}$alkyl' or '$C_{1-6}$alkoxy' as a group or part of a group means that the group is straight or branched and consists of 1 to 6 carbon atoms. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy. The term 'halogen' within the definition of $R^2$ means fluorine, chlorine, bromine or iodine.

In the compounds of general formula (I), the term 'acyl' as a group or part of a group means an alkanoyl group such as acetyl or pivaloyl.

A preferred group of compounds of general formula (I) is that wherein the substituent of formula

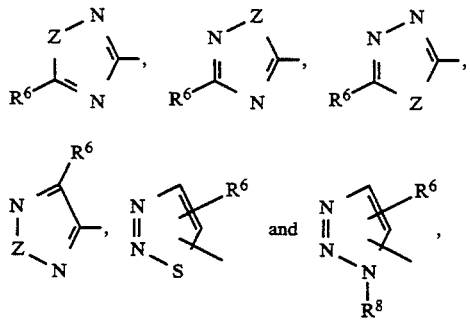

as defined above, on the phenyl group of $R^2$ is attached at a position meta or para to the bond to the phenyl ring A in general formula (I).

A further preferred group of compounds of general formula (I) is that wherein the substituent of formula

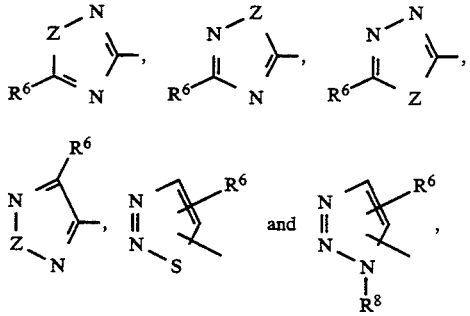

on the phenyl group of $R^2$ is attached at the position para to the bond to the phenyl ring A in general formula (I).

Another preferred group of compounds of general formula (I) is that wherein $R^2$ is additionally substituted by one or two substituents selected from halogen atoms, $C_{1-6}$alkoxy, hydroxy and $C_{1-6}$alkyl, which is (are) attached at a position ortho to the bond to the phenyl ring A in general formula (I).

A further preferred group of compounds of general formula (I) is that wherein $R^2$ represents a phenyl group substituted by the substituent

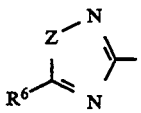

and optionally further substituted by one or two substituents selected from halogen atoms, $C_{1-6}$alkoxy, hydroxy and $C_{1-6}$alkyl.

Also preferred are those compounds of general formula (I) wherein $R^1$ represents a hydrogen atom or a $C_{1-6}$alkyl, especially methyl, group.

Another preferred group of compounds of general formula (I) is that wherein Z represents an oxygen atom.

A further preferred group of compounds of general formula (I) is that wherein $R^6$ represents a $C_{1-6}$alkyl, especially methyl, group optionally substituted by a $C_{1-6}$alkoxy, especially methoxy, group.

Also preferred is the group of compounds of general formula (I) wherein $R^4$ is attached at the para-position relative to the amide linkage.

Another preferred group of compounds of general formula (I) is that wherein $R^4$ is a halogen atom, especially a fluorine or chlorine atom, or a hydroxy or $C_{1-6}$alkoxy, especially methoxy, group.

A further preferred group of compounds of general formula (I) is that wherein $R^5$ is a hydrogen atom.

A yet further preferred group of compound of general formula (I) is that wherein $R^7$ is a $C_{1-3}$alkyl, especially methyl, group.

A particularly preferred compound of general formula (I) is: N-[4-methoxy-3-(4-methyl-1-piperazinyl)-phenyl]-2'-methyl-4,-(5-methyl -1,2,4-oxadiazol-3-yl)[1,1'-biphenyl]-4-carboxamide; and its physiologically acceptable salts and solvates.

Other preferred compounds of general formula (I) include:

N-[4-methoxy-3-(4-methyl-1-piperazinyl)phenyl]-2'-methyl-4'-(3-methyl -1,2,4-oxadiazol-5-yl)[1,1'-biphenyl]-4-carboxamide;

N-[4-methoxy-3-(4-methyl-1-piperazinyl)phenyl]-2'-methyl-4'-(5-methyl -1,3,4-oxadiazol-2-yl)[1,1'-biphenyl]-4-carboxamide;

N-[4-methoxy-3-(4-methyl-1-piperazinyl)phenyl]-2'-methyl-5'-(5-methyl -1,3,4-oxadiazol-2-yl)[1,1'-biphenyl]-4-carboxamide;

N-[4-methoxy-3-(4-methyl-1-piperazinyl)phenyl]-[4'-[5-(methoxymethyl) -1,2,4-oxadiazol-3-yl]-2'-methyl][1,1'-biphenyl]-4-carboxamide;

N-[4-methoxy-3-(4-methyl-1-piperazinyl)phenyl]-2-methyl-4'-(5-methyl -1,2,4-oxadiazol-3-yl)[1,1'-biphenyl]-4-carboxamide;

and their physiologically acceptable salts and solvates.

Further preferred compounds of general formula (I) include:

4'-[3-(Dimethylamino)-1,2,4-oxadiazol-5-yl]-N-[4-methoxy-3-(4-methyl -1-piperazinyl)phenyl]-2'-methyl[1,1'-biphenyl]-4-carboxamide;

N-[4-Methoxy-3-(4-methyl-1-piperazinyl)phenyl]-4'-(5-methyl-1,2,4-oxadiazol -3-yl)[1,1'-biphenyl]-4-carboxamide;

N-[4-Methoxy-3-(4-methyl-1-piperazinyl)phenyl]-4'-(1-methyl-1H-1,2,3-triazol -4-yl)[1,1'-biphenyl]-4-carboxamide;

N-[4-Methoxy-3-(4-methyl-1-piperazinyl)phenyl]-2'-methyl-4'-[[5-(methylsulphonyl) methyl]-1,2,4-oxadiazol-3-yl][1,1,-biphenyl]-4-carboxamide;

N-[4-Methoxy-3-(4-methyl-1-piperazinyl)phenyl]-2'-methyl-4'-(5-methyl -1,3,4-thiadiazol-2-yl)[1,1'-biphenyl]-4-carboxamide;

4'-[5-(Hydroxymethyl)-1,2,4-oxadiazol-3-yl]-N-[4-methoxy-3-(4-methyl -1-piperazinyl)phenyl]-2'-methyl[1,1'-biphenyl]-4-carboxamide;

and their physiologically acceptable salts and solvates.

Particularly preferred compounds of general formula (I) include:

N-[4-Chloro-3-(4-methyl-1-piperazinyl)phenyl]-2'-methyl-4'-(5-methyl -1,2,4-oxadiazol-3-yl)[1,1'-biphenyl]-4-carboxamide;

N-[4-Methoxy-3-(4-methyl-1-piperazinyl)phenyl]-2'-methyl-4'-(3-methyl -1,2,4-thiadiazol-5-yl)[1,1'-biphenyl]-4-carboxamide;

2'-Chloro-N-[4-methoxy-3-(4-methyl-1-piperazinyl)-phenyl]-4'-(5-methyl -1,3,4-oxadiazol-2-yl)[1,1'-biphenyl]-4-carboxamide;

N-[4-Methoxy-3-(4-methyl-1-piperazinyl)phenyl]-2'-methyl-4'-(1,2,3-thiadiazol -4-yl)[1,1'-biphenyl]-4-carboxamide;

2'-Methyl-N-[4-methyl-3-(4-methyl-1-piperazinyl)-phenyl]-4'-(5-methyl -1,3,4-oxadiazol-2-yl)[1,1'-biphenyl]-4-carboxamide;

4'-(1,5-Dimethyl-1H-1,2,4-triazol-3-yl)-N-[4-methoxy-3-(4-methyl -1-piperazinyl)phenyl]-2'-methyl[1,1'-biphenyl]-4-carboxamide;

2-Chloro-N-[4-methoxy-3-(4-methyl-1-piperazinyl)-phenyl]-4'-(5-methyl -1,2,4-oxadiazol-3-yl)[1,1'-biphenyl]-4-carboxamide;

N-[2-Fluoro-4-methoxy-5-(4-methyl-1-piperazinyl)-phenyl]-2-methyl-4'-[5-methyl-1,2,4-oxadiazol-3-yl][1,1'-biphenyl]-4-carboxamide;

N-[4-Chloro-3-(4-methyl-1-piperazinyl)phenyl]-2'-methyl-4'-(5-methyl -1,3,4-oxadiazol-2-yl)[1,1'-biphenyl]-4-carboxamide;

N-[4-Bromo-3-(4-methyl-1-piperazinyl)phenyl]-2'methyl-4'-[5-methyl-1,2,4-oxadiazol-3-yl][1,1'-biphenyl]-4-carboxamide;

N-[4-Methoxy-3-(4-methyl-1-piperazinyl)phenyl]-2'-methyl-4'-(1,3,4-oxadiazol -2-yl)[1,1'-biphenyl]-4-carboxamide;

and their physiologically acceptable salts and solvates.

5-Hydroxytryptamine (serotonin) is a neurotransmitter which is widely distributed within the central nervous system (CNS), platelets and the gastrointestinal tract. Changes in transmission in serotonergic pathways in the CNS are known to modify, for example, mood, psychomotor activity, appetite, memory and blood pressure. Release of 5-hydroxytryptamine from platelets can mediate vasospasm while changes in free 5-hydroxytryptamine levels in the gastrointestinal tract can modify secretion and motility.

Abundant pharmacological studies have led to the discovery of multiple types of receptors for 5-hydroxytryptamine, thus providing a molecular basis to the diversity of its actions. These receptors are classed as 5-HT$_1$, 5-HT$_2$ and 5-HT$_3$, with 5-HT$_1$ receptors being sub-classified as 5-HT$_{1A}$, 5-HT$_{1B}$, 5-HT$_{1C}$, 5-HT$_{1D}$ and 5-HT$_{1D}$(like) receptors. The identification of these classes and sub-classes of receptor is based mainly on radiological binding studies.

Compounds having a selective antagonist action at 5-HT$_{1D}$ receptors such as those described herein may exhibit a beneficial effect on subjects suffering from CNS disorders.

Accordingly, in a further aspect of the present invention, there is provided a method of treating a patient suffering from a CNS disorder, which method comprises administering to the patient an effective amount of a 5-HT$_{1D}$ antagonist. The patient is preferably a human patient.

In another aspect of the present invention, there is provided a 5-HT$_{1D}$ antagonist for use in the manufacture of a medicament for the treatment of a CNS disorder.

In the present specification, a 5-HT$_{1D}$ antagonist is a non-naturally occurring (synthetic) compound that specifically and selectively antagonises 5-HT$_{1D}$ receptors, i.e.—blocks the specific actions of 5-hydroxytryptamine mediated by the 5-HT$_{1D}$ receptor. Such compounds may be identified by a high level of affinity (pKi$\geq$8) in the in vitro human cortex and guinea-pig striatum radioligand binding assays described by Hoyer et al, Neuroscience Letters, 1988, 85, p357–362. Activity at 5-HT$_{1D}$ receptors may be confirmed in vivo using the guinea pig rotation model described by G A Higgins et al, Br. J. Pharmacol., 1991, 102, p305–310.

A 5-HT$_{1D}$ antagonist for use in the present method of treatment must be selective for 5-HT$_{1D}$ receptors. In the present specification, this means that the 5-HT$_{1D}$ antagonist must be 30 or more times more selective for 5-HT$_{1D}$ receptors than 5-HT$_{1A}$, 5-HT$_{1C}$ or 5-HT$_2$ receptors.

According to this definition the affinity of a compound for 5-HT$_{1A}$, 5-HT$_{1C}$ and/or 5-HT$_2$ receptors is measured using the in vitro tests described in the following publications:

5-HT$_{1A}$ Gozlan et al, Nature, 1983, 305, p140–142
5-HT$_{1C}$ Pazos et al, Eur. J.Pharmacol., 1984, 106, p531–538
5-HT$_2$ Humphrey et al, Br. J. Pharmacol, 1988, 94, p1123–1132 (rabbit aorta model).

Thus, for example, compounds of the present invention have been shown to inhibit 5-hydroxytryptamine induced contraction of the dog isolated saphenous vein and to antagonise the 5-hydroxytryptamine induced inhibition of neurotransmission in central and peripheral neurones.

5-HT$_{1D}$ Antagonists, and in particular the compounds of the present invention, may therefore be of use in the treatment of CNS disorders such as mood disorders, including depression, seasonal affective disorder and dysthymia; anxiety disorders, including generalised anxiety, panic disorder, agoraphobia, social phobia, obsessive compulsive disorder and post-traumatic stress disorder; memory disorders, including dementia, amnestic disorders and age-associated memory impairment; and disorders of eating behaviour, including anorexia herrosa and bulimia herrosa. Other CNS disorders include Parkinson's disease, dementia in Parkinson's disease, neuroleptic-induced parkinsonism and tardive dyskinesias, as well as other psychiatric disorders.

5-HT$_{1D}$ Antagonists, and in particular compounds of the present invention, may also be of use in the treatment of endocrine disorders such as hyperprolactinaemia, the treatment of vasospasm (particularly in the cerebral vasculature) and hypertension, as well as disorders in the gastrointestinal tract where changes in motility and secretion are involved. They may also be of use in the treatment of sexual dysfunction.

Therefore, according to a second aspect of the invention, we provide a compound of general formula (I) or a physiologically acceptable salt or solvate thereof for use in therapy.

According to a further aspect of the present invention, we provide a compound of general formula (I) or a physiologically acceptable salt or solvate thereof for use in the treatment of the aforementioned disorders.

According to another aspect of the invention, we provide the use of a compound of general formula (I) or a physiologically acceptable salt or solvate thereof for the manufacture of a therapeutic agent for the treatment of the aforementioned disorders.

According to a further aspect of the invention, we provide, a method of treating the aforementioned disorders which comprises administering an effective amount to a patent in need of such treatment of a compound of general formula (I) or a physiologically acceptable salt or solvate thereof.

In particular, according to another aspect of the invention, we provide a compound of general formula (I) or a physiologically acceptable salt or solvate thereof for use in the treatment or prophylaxis of depression.

It will be appreciated that the compounds according to the invention may advantageously be used in conjunction with one or more other therapeutic agents, for instance, different antidepressant agents such as tricyclic antidepressants (e.g. amitriptyline, dothiepin, doxepin, trimipramine, butriptyline, clomipramine, desipramine, imipramine, iprindole, lofepramine, nortriptyline or protriptyline), monoamine oxidase inhibitors (e.g. isocarboxazid, phenelzine or tranylcyclopramine) or 5-HT reuptake inhibitors (e.g. fluvoxamine, sertraline, fluoxetine or paroxetine), and/or antiparkinsonian agents such as dopantinergic antiparkinsonian agents (e.g. levodopa, preferably in combination with a peripheral decarboxylase inhibitor e.g. benserazide or carbidopa, or a dopamine agonist e.g. bromocriptine, lysuride or pergolide). It is to be understood that the present invention covers the use of a compound of general formula (I) or a physiologically acceptable salt or solvate thereof in combination with one or more other therapeutic agents.

Thus there is provided in a further or alternative aspect of the present invention a compound of general formula (I) or a physiologically acceptable salt or solvate thereof and an antidepressant agent in the presence of each other in the human or non-human animal body for use in the treatment of the aforementioned disorders.

In a particular aspect of the present invention there is provided a compound of general formula (I) or a physiologically acceptable salt or solvate thereof and an antiparkinsonian agent such as a dopaminergic antiparkinsonian agent, e.g. levodopa, and a peripheral decarboxylase inhibitor, e.g. benserazide or carbidopa, or a dopamine agonist e.g. bromocriptine, lysuride or pergolide in the presence of each other in the human or non-human animal body for use in the treatment of Parkinson's disease, dementia in parkinsonism, neuroleptic induced parkinsonism and tardive dyskinesias.

In using a compound of general formula (I) or a physiologically acceptable salt or solvate thereof and one or more therapeutic agents it may be preferable to employ the active ingredients in the form of separate pharmaceutical formulations. A combined formulation can be used, however, in such a combined formulation the active ingredients must of course be stable and mutually compatible in the particular formulation employed.

It will be appreciated that administration of the active ingredients to a human or non-human patient may be simultaneous, separate or sequential. Where administration is not simultaneous, the delay in administering the second of the active ingredients should not be such as to lose the beneficial effect of the combination.

While it is possible that a compound of general formula (I) may be administered as the raw chemical it is preferable to present the active ingredient as a pharmaceutical formulation.

The compounds of general formula (I) and their physiologically acceptable salts and solvates may be formulated for administration in any convenient way, and the invention therefore also includes within its scope pharmaceutical compositions comprising at least one compound of general formula (I) or a physiologically acceptable salt or solvate thereof. Such compositions may be presented for use in a conventional manner in admixture with one or more physiologically acceptable carriers or excipients.

The carrier(s) must be "acceptable" in the sense of being compatible with the other ingredients of the formulation and not deleterious to the recipient thereof.

Thus, the compositions according to the invention may be formulated for oral, buccal, parenteral or rectal administration or in a forth suitable for administration by inhalation or insufflation. Oral administration is preferred.

Tablets and capsules for oral administration may contain conventional excipients such as binding agents, for example, syrup, acacia, gelatin, sorbitol, tragacanth, mucilage of starch or polyvinylpyrrolidone; fillers, for example, lactose, sugar, microcrystalline cellulose maize-starch, calcium phosphate or sorbitol; lubricants, for example, magnesium stearate, stearic acid, talc, polyethylene glycol or silica; disintegrants, for example, potato starch or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methylcellulose, glucose/sugar syrup, gelatin, hydroxypropyl methylcellulose, carboxymethylcellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; and preservatives, for example, methyl or propyl p-hydroxybenzoates or sorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by bolus injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder forth for constitution with a suitable vehicle, e.g. sterile, pyrogen-free water, before use.

For administration by inhalation either orally or nasally the compositions according to the invention are conveniently delivered in the form of an aerosol spray presentation from pressurised packs with the use of a suitable propellant, e.g. dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation the compositions according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

The pharmaceutical formulations according to the invention may also contain other active ingredients such as antimicrobial agents, or preservatives.

The compositions according to the invention may be prepared by mixing the various ingredients using conventional means.

It will be appreciated that the amount of a compound of general formula (I) required for use in treatment will vary not only with the particular compound selected but also with the route of administration, the nature of the condition being treated and the age and condition of the patient and will ultimately be at the discretion of the attendant physician or veterinarian. In general, however, a proposed dose of the compounds of the invention for administration in man is 0.5 to 1000 mg, preferably 1 to 200 mg of the active ingredient per unit dose which could be administered, for example, 1 to 4 times per day.

The compounds of the invention may be prepared by a nun%her of processes as described in the following. In describing the processes which may be used for preparing the compounds of general formula (I) or intermediates useful in the preparation thereof, any of $R^1$–$R^{11}$, Z and k in the various formulae are as defined in general formula (I) unless otherwise stated.

It will be appreciated that in the following methods for the preparation of compounds of general formula (I), for certain reaction steps it may be necessary to protect various reactive substituents in the starting materials for a particular reaction and subsequently to remove the protecting group. Such protection and subsequent deprotection may be particularly pertinent where $R^7$, $R^8$, $R^9$ and/or $R^{10}$ in intermediates used to prepare compounds of general formula (I) are hydrogen atoms. Standard protection and deprotection procedures can be employed, for example formation of a phthalimide (in the case of a primary amine), benzyl, trityl, benzyloxycarbonyl or trichloroethoxycarbonyl derivatives. Subsequent removal of the protecting group is achieved by conventional procedures. Thus a phthalimide group may be removed by treatment with hydrazine or a primary amine, for example methylamine. Benzyl or benzyloxycarbonyl groups may be removed by hydrogenolysis in the presence of a catalyst e.g. palladium, and trichloroethoxycarbonyl derivatives may be removed by treatment with zinc dust. Trityl groups may be removed under acidic conditions using standard procedures.

It may also be necessary in some cases to protect carboxylic acid groups (e.g. as esters) or aldehyde or ketone groups (e.g. as acyclic or cyclic acetals or ketals or as thioacetals or thioketals). Subsequent removal of these protecting groups is achieved by conventional procedures. Thus for example alkyl esters may be removed under conditions of acidic or basic hydrolysis, benzyl esters may be removed by hydrogenolysis in the presence of a catalyst e.g. palladio. Acyclic or cyclic acetals or ketals may be removed under conditions of acidic hydrolysis and thioacetals and thioketals may be removed using a mercuric salt.

Hydroxyl groups may also need protection and these may be adequately protected under amenable conditions as their esters or trialkylsilyl, tetrahydropyran and benzyl ethers. Such derivatives may be deprotected by standard procedures.

According to one general process (1), the compounds of general formula (I) may be prepared by a carbonylation reaction involving an aniline (II)

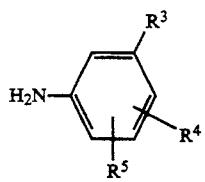

(where $R^3$, $R^4$ and $R^5$ are as defined in general formula (I)) and a halophenyl compound (III)

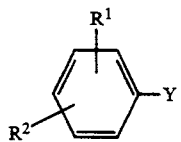

(where Y represents a halogen atom e.g. bromine or iodine or the group —$OSO_2CF_3$, and $R^1$ and $R^2$ are as defined in general formula The reaction takes place, for example, in the presence of carbon monoxide using a palladium salt as a catalyst. The reaction is effected in the presence of a suitable base e.g. a trialkylantine such as triethylamine or tri-n-butylamine and may be conducted in a suitable solvent such as an amide e.g. dimethylformamide or a nitrile e.g. acetonitrile at a temperature within the range of —100° C. to +1500° C.

Suitable palladium salts for the reaction include triarylphosphine palladium (II) salts such as bis(triphenylphosphine)palladium (II) chloride.

According to another general process (2), the compounds of general formula (I) may be prepared by treating a compound of formula (IV)

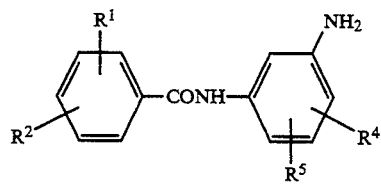

with an amine dihalide of formula (V)

$R^7N(CH_2CH_2Hal)_2$         (V)

(where Hal is a chlorine, bromine or iodine atom).

The reaction may conveniently take place in the presence of a polar solvent such as an alcohol (e.g. n-butanol) or a nitrile (e.g acetonitrile), optionally in the presence of a base, for example, an alkali metal carbonate such as sodium carbonate or potassium carbonate, or alternatively in a non-polar solvent (e.g. chlorobenzene) in the absence of a base. The reactions may conveniently be carried out at an elevated temperature, for example, reflux.

According to another general process (3), the compounds of general formula (I) may be prepared by reacting an aniline of formula (II) with an activated carboxylic acid derivative of formula (VI)

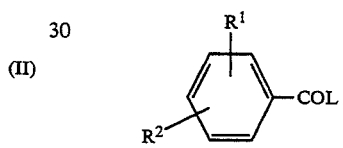

(where L is a leaving group).

Suitable activated carboxylic acid derivatives represented in formula (VI) include acyl halides (e.g. acid chlorides) and acid anhydrides including mixed anhydrides (e.g. acid formic anhydride). These activated derivatives may be formed from the corresponding acid of formula (VII)

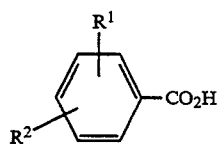

by well known procedures. For example, acid chlorides may be prepared by reaction with phosphorus pentachloride, thionyl chloride or oxalyl chloride and acid anhydrides may be prepared by reaction with an appropriate acid anhydride (e.g. trifluoroacetic anhydride), an acid chloride (e.g. acetyl chloride), an alkyl or aralkyl haloformate (e.g. ethyl or benzyl chloroformate) or methanesulphonyl chloride.

Activated carboxylic acid derivatives of formula (VI) may also be prepared in situ by the reaction of the corresponding acids of formula (VII), with a coupling reagent such as carbonyldiimidazole, dicyclohexylcarbodiimide or diphenylphosphorylazide.

The conditions under which the activated carboxylic acid derivatives of formula (VI) are formed and subsequently reacted with the anilines of formula (II) will depend upon the nature of the activated derivative. However, in general the reaction between the compounds (II) and (VI) may be carried out in a non-aqueous medium such as, for example, dimethylformamide, tetrahydrofuran, acetonitrile or a halohydrocarbon such as dichloromethane at a temperature within the range −250° C. to +1500° C. The reaction may optionally be carried out in the presence of a base such as triethylamine or pyridine and the base may also be used as the solvent for reaction.

Where acid chlorides are used, the reaction may be carried out using the Schotten-Baumann technique in the presence of a suitable base, for example, aqueous sodium hydroxide, conveniently at a temperature between 0° C. and 100° C., for example, room temperature.

According to another general process (4a), the compounds of general formula (I) may be prepared by treating a compound of formula (VIIIa)

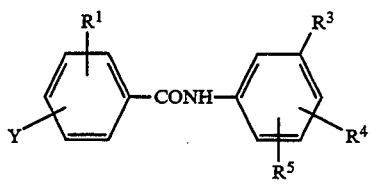

(VIIIa)

(where Y represents a bromine or iodine atom or the group —OSO$_2$CF$_3$) with a compound of formula (IXa)

 (IXa)

or an ester or an anhydride thereof.

Alternatively, according to the general process (4b), the compounds of general formula (I) may be prepared by treating a compound of formula (VIIIb)

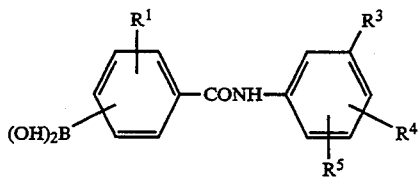

(VIIIb)

or an ester or an anhydride thereof, with a compound of formula (IXb)

R$^2$-Y    (IXb)

where Y represents a bromine or iodine atom or the group —OSO$_2$CF$_3$.

Both reactions may be effected in the presence of a transition metal catalyst such as (Ph$_3$P)$_4$Pd (where Ph represents phenyl) in a suitable solvent such as an ether (e.g. 1,2-dimethoxyethane or tetrahydrofuran) in the presence or absence of water, or an aromatic hydrocarbon (e.g. benzene). The reaction is preferably carried out in the presence of a base such as an alkali or alkaline earth metal carbonate (e.g. sodium carbonate) at a suitable temperature up to reflux.

Compounds of general formula (I) in which R$^2$, R$^4$ and R$^5$ have a particular meaning may be converted into another compound of the invention by standard methods of interconversion.

For instance, when R$^2$ contains a hydroxy or alkoxy group and/or when R$^4$ and/or R$^5$ represents hydroxy or alkoxy these groups may be interchanged by standard methods of 0-alkylation or 0-dealkylation. Thus, for example, a compound in which R$^4$ represents hydroxy may be prepared by treating a corresponding compound in which R$^4$ represents methoxy with a reagent system capable of removing the methyl group e.g. a mercaptide such as sodium ethylmercaptide in a solvent such as dimethylformamide, lithium iodide in collidine, boron tribromide in a halohydrocarbon solvent e.g. methylene chloride or molten pyridine hydrochloride.

Intermediates of formula (II) may be prepared from the corresponding compound of formula (X)

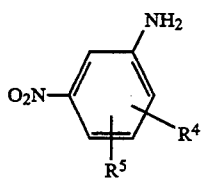 (X)

by reaction with a compound of formula (XI)

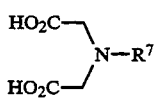 (XI)

in the presence of acetic anhydride, followed by reduction of the diketopiperazine intermediate thus formed using, for example borane. The reaction may be carried out at a temperature between 50° C. and reflux, and optionally in a solvent such as an ether, e.g, tetrahydrofuran, or toluene. The nitro group may be subsequently converted into an amine using standard methodology.

Alternatively, intermediates of formula (II) in which R$^4$ is adjacent to R$^3$, and R$^5$ is a hydrogen atom, may be prepared by nitration of a compound of formula (XII)

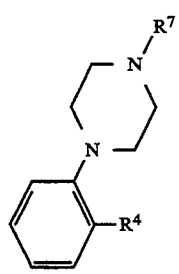 (XII)

using an appropriate nitrating system such as sulphuric acid and potassium nitrate, or nitronium tetrafluoroborate, in the presence of a solvent, for example, acetonitrile, or alternatively, where R$^7$is not a hydrogen atom, by nitrosation using, for example, sodium nitrite and a suitable acid such as sulphuric acid in a solvent, for example, water, followed in each case by reduction of the nitro or nitroso group using standard methodology.

Intermediates of formula (IV) may be prepared by reduction of the corresponding nitro compound of general formula (XIII)

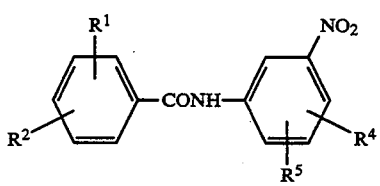 (XIII)

The reduction may be effected by catalytic hydrogenation using a metal catalyst such as palladium or platinum or oxides thereof, preferably, in a solvent such as an alcohol e.g ethanol, or alternatively by using Raney nickel and hydrazine in a solvent such as an alcohol e.g. ethanol.

Intermediates of formula (XIII) may be prepared by condensing a compound of formula (VI) with a compound of formula (X) under the conditions of general process (3).

It will be appreciated that, where necessary, a halogen substituent may be converted into a carboxyl group using standard methodology thus, for example, intermediates of formula (VII) may be prepared from an intermediate of formula (III) by lithiation using, for example, n-butyl lithium followed by quenching with carbon dioxide.

Intermediates of formula (VIIIa) and (VIIIb) may be prepared by reaction of a compound of formula (II) with a compound of formula (XIVa) or (XIVb), respectively,

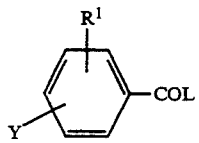
(XIVa)

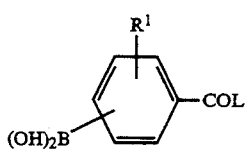
(XIVb)

according to the method of general process (3).

The boronic acid intermediates of formulae (VIIIb), (IXa) and (XIVb) or their esters or anhydrides may be used in situ under the conditions described above for general process (4).

Intermediates of formula (VII) may be prepared by the reaction of a compound of formula (IXa) or (IXb) with a compound corresponding formula (XIVa) or (XIVb) in which L represents a hydroxy group, respectively, according to the method of general process (4).

Intermediates of formula (II) may also be prepared from the corresponding carboxylic acid using conventional procedures (e.g. by Curtius rearrangement).

Intermediates of formulae (V), (X), (XI), (XII), (XIVa) and (XIVb) are either known compounds or may be prepared by standard methodology or methods analogous to those described herein.

Intermediates containing the group $R^2$ may be prepared by methods described herein and using techniques well known in the art, such as those described in "Comprehensive Organic Chemistry", Vol. 4 by D. Barton and W. D. Ollis, Pergamon Press, Oxford (1979) (see especially pages 1020–1050 for five-membered mixed heteroatom ring systems) or in "Comprehensive Heterocyclic Chemistry", Vol. 6 by A R Katritzky and C W Rees, Pergamon Press, Oxford (1984) (see pages 365–577).

Physiologically acceptable acid addition salts of the compounds of general formula (I) may be prepared by treating the corresponding free base with a suitable acid using conventional methods. Thus, for example, a generally convenient method of forming the acid addition salts is to mix appropriate quantities of the free base and the acid in an appropriate solvent e.g. an alcohol such as ethanol or an ester such as ethyl acetate.

Salts of compounds of general formula (I) may also be converted to different physiologically acceptable salts of compounds of general formula (I) using conventional methods.

The invention is illustrated but not limited by the following examples in which temperatures are in °C. Thin layer chromatography (t.l.c.) was carried out on silica plates.

The following abbreviations are used:
DMF - dimethylformamide; TEA - triethylamine; HMPA - hexamethylphosphoramide; THF - tetrahydrofuran; MSC - methanesulphonyl chloride; BTPC - bis(triphenylphosphine)palladium (II) chloride; DMA - dimethylamine; IMS - industrial methylated spirits; SPC - Short path chromatography carried out on silica (Merck 7747) unless otherwise stated. FCC - Flash column chromatography carried out on silica (Merck 9385). 'Dried' refers to drying using sodium sulphate or magnesium sulphate unless otherwise stated.

The following solvent systems were used:
System A - dichloromethane:ethanol:0.88 ammonia;
System B - dichloromethane:methanol:0.88 ammonia.

Intermediate 1

3-(4-Bromo-3-methylphenyl)-5-methyl-1,2,4-oxadiazole

A solution of sodium methoxide (1.93 g) in methanol (15 ml) was added dropwise over 10 min to a solution of hydroxylamine hydrochloride (2.48 g) in methanol (30 ml). The mixture was stirred for 1 at 20° and was then filtered. 4-Bromo-3-methylbenzonitrile (7 g) was then added to the filtrate, and the mixture heated to reflux for 18 h. The solvent was then evaporated giving a grey solid, a portion of which (2.2 g) was dissolved in acetic anhydride (6 ml) and heated to 80° for 18 h. The reaction was cooled and was poured into water (100 ml). The solid was separated, collected and recrystallised from isopropanol (20 ml) giving the title compound as colourless microcrystals (896 mg) m.p. 78°.

Intermediate 2

5-(4-Bromo-3-methylphenyl)-3-methyl-1,2,4-oxadiazole

Sodium metal (602 mg) was added to a suspension of molecular sieves (4A) in absolute ethanol (30 ml) under nitrogen at 20° . After 15 min N-hydroxyethanimidamide (1.94 g) was added. Stirring was maintained for 1 h whereupon Intermediate 8 (1 g) was added. The mixture was heated to reflux for 1.5 h, then filtered and the filtrate evaporated to dryness. The residue was dissolved in water (75 ml) and extracted with ethyl acetate (2×75 ml) and the dried extracts evaporated to give the title compound as a colourless solid (856 mg) m.p. 75°–77°.

Intermediate 3

Methyl 4-methoxy-3- (4-methyl-1-piperazinyl)benzoate hydrochloride

A suspension of 2-chloro-N-(2 -chloroethyl)-N-methylethanamine hydrochloride (1.92 g) and methyl 3-amino-4-methoxybenzoate (1.81 g) in n-butanol was refluxed with stirring for 19 h. Anhydrous sodium carbonate (0.54 g) was added and refluxing continued for 8.5 h. The solvent was then removed to give an oil which was taken up in water (50 ml) and 2N hydrochloric acid (50 ml) and extracted with ethyl acetate (2×50 ml). The acid solution was then basified with sodium bicarbonate and re-extracted with ethyl acetate (3×50 ml). The extracts were dried and concentrated to a semi-solid (2.47 g) which was absorbed from System A (200:8:1) (5 ml) onto Kieselgel G (100 g). Elution with the same solvent gave starting material and minor basic impurities. Further elution with System A (100:8:1) (450 ml) gave first minor impurities and later fractions afforded the free base of the desired product as a gum (0.48 g). This was taken up in methanol (5 ml), filtered and treated with ethereal hydrogen chloride and diluted to 25 ml with ethyl acetate. A cream coloured solid separated, was filtered and the solid (0.586 g) recrystallised from methanol:ethyl acetate to give the title compound m.p. 202°–204° C.

Intermediate 4

4-Methoxy-3-(4-methyl-1-piperazinyl)benzoic acid hydrazide

The free base of Intermediate 3 (2 g) in methanol (20 ml) was treated with hydrazine hydrate (4 ml) and refluxed under nitrogen for 16 h. The solution was evaporated and then adsorbed from ethanol onto silica gel [Merck Art. 7734, 5 g]. Purification by SPC eluting with System A (91:9:0.9) gave the title compound as an off-white solid (0.764 g).

T.l.c. System A (90:10:0.1), Rf 0.2.

Intermediate 5

4-Methoxy-3-(4-methyl-1-piperazinyl)benzenamine

A solution of Intermediate 4 (0.73 g) in water (30 ml) was mixed with concentrated hydrochloric acid (0.6 ml), the solution cooled to 0 to 5° C. and a solution of sodium nitrite (0.219 g) in water (10 ml) added during 5 min. The solution was stirred at 0°–5° C. for 20 min, then 1 h at 23° C., and treated with concentrated hydrochloric acid (40 ml) and acetic acid (40 ml). The mixture was heated at reflux for 2 h, cooled and poured into aqueous sodium hydroxide (5N; 260 ml). The mixture was extracted with ethyl acetate (3×500 ml), and the combined, dried organic extracts were evaporated to give the title compound as a gum (0.190 g).

T.l.c. System A (95:5:0.5), Rf 0.2. Intermediate 5 was also made by the alternative two-step reaction as follows:

(a) 1-Methyl-4-(2-methoxy-5-nitrophenyl)piperazine 1-(2-Methoxyphenyl)-4-methylpiperazine (5.36 g) was acidified with 5N sulphuric acid and the excess water evaporated in vacuo. Concentrated sulphuric acid (95–98%, 22 ml) was added and the mixture stirred at room temperature until homogeneous. To the stirred, dark solution was added portionwise at room temperature potassium nitrate (3.07 g) in ten portions at intervals of approximately 5 min. The mixture was stirred at room temperature for 4 h then poured onto ice (~500 ml) and the mixture made slightly alkaline with anhydrous sodium carbonate. The basic mixture was extracted with ethyl acetate (4×150 ml) and the combined extracts dried. After 1 h the mixture was filtered and the filtrate evaporated to dryness in vacuo. The dark red residue was diluted with ether (200 ml) and the solid which separated (0.51 g) was filtered off and discarded. The filtrate was evaporated to dryness and the oily residue mixed with ether (300 ml) and the suspension filtered. The filtrate was evaporated to dryness to give a red gum which very slowly solidified to give the title compound (5.45 g)

T.l.c System A (150:8:1), Rf 0.45

(b) 4-Methoxy-3-(4-methyl-1-piperazinyl)benzeneamine

To a solution of the product of step (a) (5.07 g) in ethanol (70 ml) was added a paste of Raney Nickel in water (2 g). To the warmed suspension was added, with constant agitation, hydrazine hydrate (5 ml) dropwise during 20 min with occasional warming. After the main effervescence had ceased, the suspension was heated for 15 min and then filtered with the aid of ethanol under nitrogen. The residues were kept moist and washed with ethanol and the combined filtrate and washings were evaporated to dryness with the aid of ethanol. The dark residue was re-evaporated with ethanol (20 ml), resuspended in ether (40 ml) and the mixture filtered. The residue was washed with ether and dried to give a solid consisting of the title compound (2. 365 g)

T.l.c System A (70:8:1), Rf 0.25.

Intermediate 6

4-Bromo-N-[4-methoxy-3-(4-methyl-1-piperazinyl)-phenyl]benzamide

A solution of Intermediate 5 (0.168 g) in pyridine (3 ml) was treated with 4-bromobenzoyl chloride (0.25 g) and stirred at 110°, under nitrogen, for 5 h. Sodium bicarbonate (20 ml; 8%) was added and the mixture was evaporated. The residue was pre-adsorbed onto silica gel [Merck Art. 7734 c.a. 5 g] and purified by SPC eluting with System A (97:3:0.3) to give the title compound as a beige solid (0.237 g), m.p. 158.5°–159.5° C.

Intermediate 7

[4-[[[4-Methoxy-3-(4-methyl-1-piperazinyl)phenyl]amino]carbonyl]phenyl]boronic acid n-Butyllithium (7.5 ml of 1.6M solution in hexane) was added dropwise at −90° to −100° to a stirred solution of Intermediate 6 (404 mg) and triisopropylborate (2.77 ml) in dry THF (20 ml) over 45 min under nitrogen, and stirring continued for 1.5 h at -90° to −103° for 1.5 h. After 3 h at −78°, the cooling bath was removed and the mixture stirred at +23° for 11 h. Water (4 ml) was added, and, after lb, the mixture was evaporated. The residue was adsorbed from System A (50:45:5) onto silica gel (Merck 7734, 10 ml) and purified by FCC eluting with System A (89:10:1→50:45:5) to give firstly recovered impure starting material followed by the title compound as a cream foam (280 mg)

T.l.c. System A (50:45:5) Rf 0.04.

Intermediate 8

Methyl 4-bromo-3-methylbenzoate

4-Bromo-3-methylbenzoic acid (10 g) was suspended in methanol (50 ml) containing conc. sulphuric acid (2 ml). The mixture was heated to reflux for 18 h. On addition of 8% NaHCO$_3$ (100 ml) to the cooled reaction, a solid was formed which was collected by filtration. Drying in vacuo at 40°–45° gave the title compound as a liquid which recrystallised on cooling (10.25 g) m.p. 39.5°–40.5° C.

Intermediate 9

4-Bromo-3-methylbenzoic acid hydrazide

A solution of Intermediate 8 (2 g) in methanol (20 ml) containing hydrazine hydrate (1.1 ml) was heated to reflux for 18 h. On cooling a solid crystallised which was collected by filtration and washed with ether to give the title compound as colourless needles (1.81 g), m.p. 164°–166° C.

Intermediate 10

2-(4-Bromo-3-methylphenyl)-5-methyl-1,3,4-oxadiazole

Intermediate 9 (1 g) in 1,1,1-triethoxyethane (10 ml) was heated to reflux for 18 h. The mixture was then allowed to cool and the title compound collected by filtration as a colourless powder (816 mg) m.p. 135°–137° C.

Intermediate 11

2-(3-Bromo-4-methylphenyl)-5-methyl-1,3,4-oxadiazole

A solution of Intermediate 8 (2 g) in methanol (20 ml) containing hydrazine hydrate (1.1 ml) was heated to reflux under nitrogen for 18 h. On cooling a crystalline solid was deposited which was collected by filtration (1.20 g). A sample of this material (1 g) was suspended in triethylorthoacetate (10 ml) and was heated to reflux for 18 h. The mixture was left to cool and the crystalline title compound collected by filtration (535 mg) m.p. 91°–3°.

Intermediate 12

3-(4-Bromo-3-methylphenyl)-5-(methoxymethyl)-1,2,4-oxadiazole

A solution of sodium methoxide (740 mg) in methanol (10 ml) was added dropwise to a solution of hydroxylamine hydrochloride (950 mg) in methanol (15 ml). The mixture was stirred at 20° for 1 h and then filtered. 4-Bromo-3-methylbenzonitrile (2.68 g) was then added to the filtrate, and the mixture heated to reflux for 18 h. The solvent was then evaporated giving a grey solid (3.5 g). A sample of this material (1 g) was dissolved in dry pyridine (5 ml) and was treated dropwise with methoxyacetyl chloride (0.8 ml). The mixture was then heated at reflux for 0.5 h. The cooled mixture was poured into water (30 ml) and refrigerated for 1 week. The solid thus formed was filtered and recrystallised from isopropanol (2 ml) to give the title compound as off-white microcrystals (300 mg) m.p.52°–53.5°.

Intermediate 13

4-Bromo-N-[4-methoxy-3-(4-methyl-1-piperazinyl)phenyl-3-methylbenzamide

4-Bromo-3-methylbenzoic acid (4.86 g) in an excess of thionyl chloride (25 ml) was heated at reflux for 1 h. The excess thionyl chloride was then removed by distillation and evaporation. The resultant acid chloride was added to a mixture of a solution of Intermediate 5 (5.0 g) in THF (25 ml) and sodium hydroxide (1.8 g) in water (30 ml). After stirring, under nitrogen, overnight at room temperature the solvent was removed by evaporation, water (40 ml) added and the mixture extracted with dichloromethane (5×50 ml), dried and evaporated to give a brown/orange sticky foam. This was purified by FCC eluting with system B (970:20:10) to give the title compound (5.73 g).

T.l.C System B (970:20:10) Rf=0.11.

Intermediate 14

[4-[[[4-Methoxy-3-(4-methyl-1-piperazinyl)phenyl]amino]carbonyl]-2-methylphenyl]boronic acid Intermediate 13 (5.77 g) was treated according to the method of Intermediate 7 to give title compound (1.87 g) as a pale yellow foam. T.l.c System B (890:100:10) Rf=0.07

Intermediate 15

1-(2-Chloro-5-nitrophenyl)-4-methylpiperazine

A mixture of 2-chloro-5-nitrobenzenamine (7.95 g) and 2-chloro-N-(2-chloroethyl) -N-methylethanamine hydrochloride (8.86 g) in chlorobenzene (40 ml) under nitrogen was heated to reflux for 3 days before cooling and diluting with dichloromethane (60 ml). The reaction mixture was then extracted with water (2×500 ml), the aqueous layers combined and basified with 2N sodium hydroxide, then extracted with dichloromethane (4×400 ml). The combined, dried extracts were concentrated in vacuo to give a dark brown oil (7.82 g) which was purified by FCC eluting with ether to give a dark brown oil which crystallised upon standing. The material was dissolved in ethanol (40 ml) and boiled up with some charcoal (300 mg). The hot ethanolic suspension was filtered and concentrated in vacuo to give the title compound as a yellow oil which crystallised on standing (5.25 g) m.p.63°–64° C.

Intermediate 16

4-Chloro-3-(4-methyl-1-piperazinyl)benzenamine

A solution of Intermediate 15 (5.06 g) in ethanol (60 ml) and water (10 ml) was treated with Raney Nickel (2 g of a slurry in water) under nitrogen. This mixture was cooled to 18° C. and treated dropwise with hydrazine hydrate (4 ml) over 15 minutes. The resultant mixture was stirred at room temperature for 2 hours before filtering. The filtrate was concentrated in vacuo to give an oil which crystallised upon cooling. The pale brown crystalline solid was dried in vacuo to give the title compound as a brown crystalline solid (4.36 g) m.p 96°–97° C.

Intermediate 17

[4-[[[4-Chloro-3-(4-methyl-1-piperazinyl)Phenyl]amino]carbonyl]phenyl]boronic acid To a cooled (0°) stirred solution of (4-carboxyphenyl)boronic acid (166 mg) in dry pyridine (5 ml) was added thionyl chloride (0.08 ml). The mixture was stirred for 30 mins and then Intermediate 16 (225 mg) was added. Stirring was maintained at 20° for 18 h. Water (40 ml) was added and the mixture was washed with ethyl acetate (2×40 ml). The precipitate which formed in the aqueous layer was collected and dried to give the title compound (196 mg)

Tlc System A (10:8:1) Rf 0.1

Intermediate 18

5-(4-Bromo-3-methylphenyl)-3-methyl-1,2,4-thiadiazole

A solution of 4-bromo-3-methylbenzenecarbothioamide (1.20 g) in dimethylacetamide dimethyl acetal (2 ml) and dichloromethane (30 ml) was stirred under nitrogen at room temperature for 7 h. The solvent was evaporated in vacuo to give a dark brown oil to which was added hydroxylamine-0-sulphonic acid (0.88 g), methanol (20 ml) and pyridine (0.83 ml) and the mixture stirred at room temperature under nitrogen for 16 h. After evaporation, aqueous potassium carbonate was added and the mixture was extracted with dichloromethane. The combined extracts were dried and evaporated to give a brown residue which was purified by column chromatography on silica eluting with hexane: ethyl acetate (4:1) to give the title compound as an orange solid (0.8 g).

T.l.c.hexane:ethyl acetate (4:1), Rf=0.52

Intermediate 19

5-(4-Bromo-3-methylphenyl)-N t N-dimethyl-1,2,4-oxadiazol-3-amine

To a stirred solution of 4-bromo-3-methylbenzoic acid (500 mg) in dry acetonitrile (5 ml) containing TEA (0.48 ml) was added dropwise ethyl chloroformate (0.33 ml) under nitrogen. The mixture was stirred for 30 mins and then N,N-dimethyl-N-hydroxyguanidine, hydrochloride (486 mg) was added and stirring was maintained at 20° for 18 h. 2N sodium carbonate (30 ml) was added, and the mixture extracted with ethyl acetate (2×30 ml). The dried extracts were evaporated to give a pale yellow solid. This material was chromatographed on silica gel eluting with System A (200:8:1) to give a colourless solid (400 mg). 200 mg of this intermediate was dissolved in absolute ethanol (5 ml) and was treated with sodium methoxide (38 mg). The mixture was heated to reflux for 2 h and was then filtered to remove some inorganic solid. The solvent was then evaporated giving a cream solid which was chromatographed on silica gel eluting with hexane:dichloromethane (1:2) to give the title compound as an off-white solid (62 mg).

T.l.c. System A (100:8:1) Rf 0.58

Intermediate 20

2-Chloro-4-(5-methyl-1,3,4-oxadiazol-2-yl)phenyl

A mixture of 3-chloro-4-hydroxybenzoic acid hydrazide (6 g) and 1,1,1-triethoxyethane (90 ml) was refluxed under nitrogen for 19.5 h. On cooling and stirring, the solid which crystallised out of the reaction mixture was filtered off, washed well with ethyl acetate and dried to give the title compound (1.8 g)

T.l.c. ethanol Rf 0.65.

Intermediate 21

2-Chloro-4-(5-methyl-1,3,4-oxadiazol-2-yl)phenol trifluoromethanesulphonate ester Trifluoromethanesulphonic anhydride (0.95 ml) was added dropwise to a solution of Intermediate 20 (1 g) and pyridine (0.75 ml) in dichloromethane (19 ml) at 0° C. under nitrogen. The reaction mixture was stirred at room temperature for 2 h. A further addition of trifluoromethanesulphonic anhydride (0.1 ml) was made and the reaction stirred for a further 1.0 h. The solution was poured into hydrochloric acid (1N; 100 ml), the mixture extracted with dichloromethane (3×100 ml) and the dried extract evaporated to give the title compound as a pale orange solid (1.85 g).

Assay Found: C,34.7; H,1.8; N,8.2;
$C_{10}H_6N_2O_4ClF_3S$ requires: C,35.05; H,1.8; N,8.2%.

Intermediate 22

4-(4-Bromo-3-methylphenyl)-1,2,3-thiadiazole

A mixture of 1-(4-bromo-3-methylphenyl)ethanone (500 mg) and 4-methylbenzenesulphonic acid hydrazide (437 mg) was heated to reflux in ethanol (15 ml) containing a few 4A molecular sieves for 5 h. On cooling, colourless needles were formed, which were collected by filtration (577 mg). 300 mg of this intermediate hydrazone were dissolved in thionyl chloride (2 ml) and was stirred at 20° for 5 h. The mixture was neutralised with 2N sodium carbonate (40 ml) and extracted with ethyl acetate (2×30 ml). The dried extracts were then evaporated to give a yellow solid. This material was chromatographed on silica eluting with dichloromethane;hexane (1:1) to give the title compound as pale yellow solid (167 mg).

T.l.c. ethyl acetate:hexane (1:4) Rf 0.52.

Intermediate 23

1-(2-Methyl-5-nitrophenyl)-4-methyl-2,6-piperazinedione

A suspension of N-methyliminodiacetic acid (2.00 g) in acetic anhydride (10 ml) was stirred at room temperature for 10 min and then heated to 15° C. for 1 h, after which time the solution had turned dark brown. The solution was concentrated in vacuo and 10 ml of distillate was collected. The resulting brown gum was then treated with 2-methyl-5-nitrobenzenamine (2.06 g) suspended in toluene (20 ml). The resulting mixture was heated to 100° C. for 60 min before allowing to cool overnight, giving a precipitate which was collected by filtration. The solid was washed with cold toluene (3×10 ml) and then air-dried for 2 min. The solid was then added to a flask containing acetic anhydride (15 ml), heated to 140° C. for 20 min to effect complete solution of the solid. The mixture was then allowed to cool to 60° C. before concentration, in vacuo. 10 ml of distillate was collected. The crystalline solid which formed as the residue cooled was filtered off, washed with ether, and then recrystallised from methanol (20 ml), to give the title compound as a fine powdery crystalline brown solid (1.78 g) m.p. 157°–158° C.

Intermediate 24

1-(5-Amino-2-methylphenyl)-4-methyl-2,6-piperazinedione a suspension of Intermediate 23 (1.70 g) in ethanol:water (5:2,50 ml) was added under vacuum to a suspension of 10% palladium on charcoal 50% paste (600 mg) in ethanol:water (5:2, 20 ml). The resulting suspension was stirred at room temperature under an atmosphere of hydrogen for 10 min. The suspension was filtered through hyflo, concentrated in vacuo, and the residue was dissolved in dichloromethane, dried, filtered and concentrated in vacuo to give the title compound as a cream-coloured foam (1.49 g).

T.l.c system A (150:8:1), Rf 0.41.

Intermediate 25

4-Methyl-3-(4-methyl-1-piperazinyl)benzenamine

A solution of intermediate 24 (1.48 g) in dry THF (60 ml) was heated to reflux under nitrogen, and treated dropwise with borane-THF complex (1 molar solution, 2 5.5 ml). The resulting mixture was heated at reflux under nitrogen for 22 h before cooling and treating with 2N hydrochloric acid (10 ml) very slowly. The mixture was then heated to reflux for a further 2 h before cooling to room temperature and concentrating in vacuo to a volume of 10 ml. The residue was diluted with 2N sodium carbonate (100 ml) and extracted with ethyl acetate (3×100 ml). The combined, dried extracts were concentrated in vacuo and purified by FCC eluting with System A (150:8:1) to give the title compound as a crystalline pale yellow solid (922 mg) m.p. 83°–84° C.

Analysis found: C,70.2; H,9.5; N,20.3;
$C_{12}H_{19}N_3$ requires: C,70.2; H,9.3; N,20.5%.

Intermediate 25 was also made by the alternative two-step reaction as follows:

(a) 1-Methyl-4-(2-methyl-5-nitrophenyl)piperazine

A suspension of 2-methyl-5-nitrobenzenamine (5.25 g) in chlorobenzene (40 ml) under nitrogen was treated with 2-chloro-N-(2-chloromethyl)-N-methylethanamine hydrochloride (6.64 g). The resulting mixture was heated to reflux and stirred for 20 hours before cooling to room temperature and diluting with dichloromethane (40 ml). The organic layer was extracted with slightly acidic water (2×150 ml), the combined aqueous extracts basified with 2N sodium hydroxide and then extracted with dichlormethane (3×250 ml). The combined, dried extracts were concentrated in vacuo to give a dark brown oil which was purified by FCC eluting with System A (250:8:1) to give the title compound as a yellow crystalline solid (4.59 g). m.p. 61°–62° C.

(b) 4-Methyl-3-(4-methyl-1-piperazinyl)benzenamine

A solution of the product of step (a) (4.5 g) in ethanol was added under vacuum to a prehydrogenated suspension of palladium on charcoal (10% Pd on C, 50% paste with water, 1.4 g) in ethanol: water (5:2, 50 ml). The suspension was stirred at room temperature under an atmosphere of hydrogen for 2 hours. The suspension was filtered through a pad of hyflo, the filter pad washed well with ethanol:water (4:1, 200 ml) and the combined filtrates evaporated in vacuo to give a gummy solid which was dissolved in dichloromethane, dried and concentrated in vacuo to give the title compound as a pale green crystalline solid (4.052 g) m.p. 82°–83° C.

Analysis Found: C, 70.2; H, 9.5; N,20.4.
$C_{12}H_{19}N_3$ requires: C, 70.2; H, 9.3; N, 20.5%.

Intermediate 26

4-Bromo-N-[4-methyl-3-(4-methyl-1-piperazinyl)phenyl]benzamide

A solution of 4-bromobenzoyl chloride (1.47 g) in THF (5 ml) was added to a stirred solution of Intermediate 25 (915 mg) in THF (15 ml) and water (10 ml) containing sodium hydroxide (350 mg). The mixture was stirred at room temperature under nitrogen for 2½h before adding water (50 ml) and extracting with dichloromethane (3×50 ml). The combined extracts were dried and concentrated in vacuo to give a pale yellow foam. The foam was dissolved in dichloromethane (5 ml) to give a yellow solution which solidified. Excess dichloromethane was removed in vacuo and ether was added (25 ml). The solid was triturated and then filtered and dried in vacuo at 60° C. for 2 h to give the title compound as an off-white solid (1.464 g), m.p. 208°–209° C.

Intermediate 27

Methyl 4'-[[[4-methoxy-3-(4-methyl-1-piperazinyl)phenyl]amino]carbonyl]-2-methyl[1,1'-biphenyl]-4-carboxylate A mixture of Intermediate 7 (1.1 g), Intermediate 8 (0.68 g), tetrakis (triphenylphosphine)palladium (0) (50 mg) and 2N sodium carbonate (10 ml) in DME (10 ml) was treated according to the method of Example 10 to give the title compound (1.15 g) as a pale yellow foam.

T.l.c. System A (100:8:1) Rf 0.36.

Intermediate 28

4-Bromo-3-methyl-N-hydroxybenzimidamide

A solution of 4-bromo-3-methylbenzonitrile (20.0 g) in methanol (100 ml) was treated with hydroxylamine hydrochloride (4×2.08 g) and potassium t-butoxide (4×3.25 g) over 6 hours and the resulting mixture heated at reflux for 18 h. After cooling, the reaction mixture was poured into water (800 ml), the suspension stirred for 30 min, and the white solid filtered off and dried in vacuo to give the title compound (21.2 g).

Analysis found: C,41.9; H,3.9; N,12.2.
$C_8H_9BrN_2O$ requires: C,42.0; H,4.0; N, 12.2%.

Intermediate 29

3-(4-Bromo-3-methylphenyl)-5-[(methanesulphonyl)methyl]-1,2,4-oxadiazole

A solution of Intermediate 28 (250 mg) in methanol (5 ml) was heated to reflux and was treated dropwise, simultaneously, with sodium methoxide (30% in methanol, 0.5 ml) and methyl methylsulphonylacetate (680 mg), both diluted with 3 ml methanol. Heating was continued for 3 h then the mixture was allowed to cool and was poured into water (75 ml). The flocculent yellow precipitate was filtered and dried to give the title compound (274 mg) as a cream-coloured solid m.p. 130°–132°.

Intermediate 30

4-Bromo-3-methylbenzoic acid 2-acetylhydrazide

A mixture of Intermediate 9 (1 g) in ethanol (20 ml) containing acetic anhydride (0.61 ml) and TEA (0.91 ml) was heated to reflux for 2 h. The mixture was then allowed to cool and was poured into water (150 ml). This gave a very fine precipitate which was collected and dried to give the title compound (991 mg) m.p. 186°–187°.

Intermediate 31

2-(4-Bromo-3-methylphenyl)-5-methyl-1,3,4-thiadiazole

A mixture of Intermediate 30 (450 mg) and 2,4-bis(2-methoxyphenyl)-1,3,2,4-dithiaphosphetane-2,4-disulphide (Lawesson's reagent; 840 mg) was heated to reflux in toluene (15 ml), under nitrogen, for 1 h. After cooling, the mixture was partitioned between 2N sodium carbonate (60 ml) and ethyl acetate (2×40 ml). The dried extracts were-evaporated giving a pale yellow oil. Trituration of the oil ether gave a solid which was purified by FCC eluting with ethyl acetate: hexane (1: 4 ) to give the title compound as a colourless crystalline solid (382 mg) .

T.l.c. ethyl acetate:hexane (1:2) Rf 0.30.

Intermediate 32

3-(4-Bromo-3-methylphenyl)-1,2,4-oxadiazole-5-methanol

A solution of Intermediate 28 (250 mg) in methanol (5 ml) was heated to reflux and was treated dropwise, simultaneously, with sodium methoxide (30% in methanol, 0.5 ml) and methyl hydroxyacetate (0.31 ml), both diluted with methanol (3 ml). Heating was maintained for 18 h, then the mixture was allowed to cool, and was added to water (75 ml). The cream coloured precipitate was collected and dried in vacuo to give the title compound (241 mg) m.p. 111°–112°.

Intermediate 33

3-(4-Bromo-3-methylphenyl)-5-methyl-1H-1,2,4-triazole

A mixture of Intermediate 9 (742 mg) and ethyl acetimidate, hydrochloride (600 mg) in ethanol (20 ml) containing TEA (1.35 ml) was heated to reflux, under nitrogen, for 18 h. The solvents were then evaporated and the residue purified by FCC eluting with System A (300:8:1) to give the title compound as a colourless solid (450 mg).

T.l.c. System A (100: 8: 1) Rf 0.55.

Intermediate 34

3-(4-Bromo-3-methylphenyl)-1,5-dimethyl-1H-1,2,4-triazole

To a stirred solution of Intermediate 33 (300 mg) in dry DMF (3 ml) under nitrogen was added sodium hydride (60% dispersion in oil, 52 mg). The mixture was stirred for 30 mins and then methyl iodide (0.15 ml) was added. The mixture was stirred at 20° for 1 h and then water (20 ml) was added and stirring maintained for a further 1 h. The solid which precipitated was collected and dried in vacuo to give the title compound (214 mg).

T.l.c. System A (200:8:1) Rf 0.41.

Intermediate 35

4-Fluoro-2-methoxybenzenamine

A solution of 5-fluoro-2-nitrophenol (10.0 g) in dry acetone (40 ml) under nitrogen was treated with potassium carbonate (8.9 g). The mixture formed a deep red coloured thick precipitate. Methyl iodide (5 ml, 11.4 g) was added slowly and the mixture stirred overnight and then at 60° C. for 3 hours. Further methyl iodide (3 ml, 6.84 g) was added and the mixture stirred at 60° C. for a further 3 hours. After this time the deep red colour had disappeared, and the mixture (now orange) was added to water (50 ml) and sodium hydroxide (2N, 40 ml), and extracted with dichloromethane (3×100 ml). The combined, dried extracts were concentrated in vacuo to give a yellow oil which upon cooling crystallised giving a pale yellow crystalline solid (4-fluoro-2-methoxy-1-nitrobenzene 10.88 g). A solution of this solid in ethanol:water (200 ml, 6:2) was added under vacuum to a prehydrogenated suspension of palladium (10% on carbon, 50% paste, 2.5 g) in ethanol:water (80 ml, 6:2). The suspension was stirred under an atmosphere of hydrogen for 2 hours, the suspension was filtered through Hyflo and the filtercake washed thoroughly with ethanol and water. The combined filtrates were concentrated in vacuo and the moist residue re-evaporated with ethanol. The purple oily residue was dissolved in dichloromethane (200 ml), dried and concentrated in vacuo to give the title compound as a dark purple liquid. (7.73 g).

Analysis: Found: C, 59.8; H, 6.1; N, 9.8.
$C_7H_8FNO$ requires: C,59.6; H, 5.7; N, 9.9%.

Intermediate 36

1-(4-Fluoro-2-methoxyphenyl)-4-methylpiperazine

A mixture of Intermediate 35 (7.70 g) and 2-chloro-N-(2-chloroethyl)-N-methylethanamine hydrochloride (11.7 g) in chlorobenzene (60 ml) was heated to reflux and stirred at reflux for 5 hours before cooling to room temperature and stirring for 60 hours. Heating was resumed and the reaction maintained at reflux for 5 hours, before cooling to room temperature, diluting with dichloromethane (100 ml) and extracting with water (3×100 ml). The solution was made slightly acidic with 2N hydrochloric acid, the aqueous extracts were then made basic (pH8-9) with 2N sodium hydroxide and extracted with dichloromethane (4×75 ml). The combined, dried extracts were concentrated in vacuo to give a dark brown oily residue. This was purified by FCC eluting with System A (300:8:1) and dried in vacuo to give the title compound as a dark brown oil (1.312 g).

T.l.c. System A (150:8:1) Rf=0.37

Intermediate 37

1-(4-Fluoro-2-methoxy-5-nitrophenyl)-4-methylpiperazine

Intermediate 36 (1.25 g) was added dropwise to conc. sulphuric acid (4 ml). The mixture was stirred until complete solution of material was effected, and then treated portionwise with potassium nitrate (0.712 g) using a water bath to maintain the temperature at 25° C. The resulting mixture was stirred at room temperature for 2 hours before pouring into ice (20 g). The aqueous solution was then neutralised with 0.88 aqueous ammonia and basified (pH8) with 2N sodium carbonate. The basic solution containing a gummy precipitate was extracted with dichloromethane (4×10 ml) and the combined, dried extracts concentrated in vacuo to give the title compound as a dark orange oil (1.349 g), which crystallised upon standing.

n.m.r. ($CDCl_3$) δ 2.37(3H,s), 2.61(4H,br-t), 3.09(4H,br.t), 3.97(3H,s), 6.70(1H,d), 7.62(1H,d).

Intermediate 38

2-Fluoro-4-methoxy-5-(4-methyl-1-piperazinyl)benzenamine

A solution of Intermediate 37 (1.30 g) in ethanol:water (7:2, 45 ml) was added under vacuum to a prehydrogenated suspension of palladium on charcoal (10% Pd on C, 50% paste, 480 mg) in ethanol:water (7:2, 18 ml). The resulting suspension was stirred under an atmosphere of hydrogen for 3 hours. The suspension was filtered through hyflo and the filter pad washed thoroughly with ethanol. The combined filtrates were concentrated in vacuo, the residue dissolved in dichloromethane, dried, filtered and concentrated in vacuo to give the title compound as a purplish/brown solid (1.065 g)

n.m.r. ($CDCl_3$) δ 2.35 (3H,s), 2.60 (4H,m), 3.01 (4H,m), 3.40 (2H,br.s), 3.79 (3H,s), 6.43 (1H,d), 6.60 (1H,d).

Intermediate 39

4-Bromo-N-[2-fluoro-4-methoxy-5-(4-methyl-1-piperazinyl)phenyl]-3-methylbenzamide A suspension of 4-bromo-3-methylbenzoic acid (606 mg) in thionyl chloride (3 ml) under nitrogen, was heated to reflux for 2 hours. Excess thionyl chloride was removed in vacuo, and the resulting oily residue (the acid chloride) was dissolved in THF (5 ml) and added slowly to a stirring solution of Intermediate 38 (657 mg) in THF (30 ml) and 2N sodium hydroxide (3 ml). The mixture was stirred at room temperature for 4 hours, before pouring into water (100 ml) and extracting with dichloromethane (3×100 ml). The combined, dried extracts were concentrated in vacuo to give the title compound as a brown foam (940 mg).

n.m.r. (CDCl₃) δ 2.36 (3H,s), 2.48 (3H,s), 2.62 (4H,m), 3.10 (4H,m), 3.85 (3H,s), 6.70 (1H,d), 7.52 (1H,dd), 7.65 (1H,d), 7.78 (2H,m), 7.99 (1H,d).

Intermediate 40

[4-(5-Methyl-1,2,4-oxadiazol-3-yl) phenyl]boronic acid

A solution of 3-(4-bromophenyl)-5-methyl-1,2,4-oxadiazole (1.0 g) in dry THF (8 ml) containing triisopropylborate (3.5 ml, 2.82 g) was cooled to −100° C. under nitrogen, and treated cautiously with tert-butyllithium (8.82 ml, 1.7M solution). The temperature was maintained between −90° C. and −105° C. during addition. The mixture was stirred at −100° C. for 20 mins after complete addition, and then allowed to warm to −30° C. The mixture was treated slowly with water (5 ml) and allowed to warm to room temperature, 2N sodium hydroxide (50 ml) was added and the basic aqueous layer washed with dichloromethane (2×50 ml). The aqueous layer was acidified with 2N hydrochloric acid (60 ml) and extracted with dichloromethane (4×50 ml, containing 20% methanol). The combined, dried extracts were concentrated in vacuo to give the title compound as a pale yellow solid (500 mg). m.p. 266°-268° C.

Intermediate 41

2'-Methyl-4'-(2-methyl-1,3,4,-oxadiazol-5-yl)[1,1'-biphenyl]'4'-carboxylic acid

A mixture of Intermediate 10 (610 mg) and 2N sodium carbonate (3 ml) in DME (10 ml) was treated with tetrakis(triphenylphosphine)Palladium (0) (20 mg) under nitrogen and stirred for 10 minutes before treating with 4-(carboxyphenyl)boronic acid (400 mg). The resulting mixture was heated to reflux and stirred for 24 hours before cooling to room temperature and pouring into 1N sodium carbonate (40 ml). The aqueous phase was washed with dichloromethane (100 ml) and then acidified. The acidic aqueous phase was extracted with dichloromethane:methanol (5:1, 2×50 ml) and the combined extracts dried and concentrated in vacuo to give the title compound as a white powdery solid (684 mg) m.p. 224°-225° C.

Intermediate 42

2'-Methyl-4'-(5-methyl-1,2,4-oxadiazol-3-yl)[1,1'-biphenyl]-4-carboxylic acid

A mixture of 4-(carboxyphenyl)boronic acid (150 mg), Intermediate 1 (228 mg), sodium carbonate(412 mg) and tetrakis (triphenylphosphine)palladium (0) (21 mg) in 1:1 aqueous DME (20 ml) was heated to reflux under nitrogen for 18 h. The mixture was allowed to cool, acidified with 2N hydrochloric acid and then extracted with ethyl acetate (2×40 ml). The dried extracts were evaporated to give a cream-coloured solid (285 mg). This was recrystallised from isopropanol (5 ml) giving the title compound as a fawn solid (165 mg).m.p. 229°-231°.

Intermediate 43

N-Methyl-4-(2-bromo-5-nitrophenyl)piperazine

A suspension of 2-bromo-5-nitrobenzenamine (26.0 g) and 2-chloro-N-(2-chloromethyl)-N-methylethanamine hydrochloride (23.0 g) in chlorobenzene (150 ml) was treated according to the method of Intermediate 36. Purification by FCC eluting with System A (300:8:1 gradient to 200:8:1) gave the title compound as a brown solid (9.498 g) m.p. 100°-103° C.

Intermediate 44

4-Bromo-3-(4-methyl-1-piperazinyl)benzenamine

A suspension of Intermediate 43 (8.68 g) in ethanol (80 ml) and water (20 ml), under nitrogen, was treated with Raney nickel (~3 g of a slurry with water). The suspension was then cooled to 17° C. and maintained at a temperature below 28° C. during the slow addition of hydrazine hydrate (6 ml), over 20 min. The cooled mixture was then stirred under nitrogen for 2 hours and filtered through Hyflo. The filter cake was washed thoroughly with ethanol:water (280 ml, 6:1) and the combined filtrates were concentrated in vacuo to give a gummy solid which was dissolved in dichloromethane, dried and concentrated in vacuo to give a dark grey/brown solid. The solid was triturated in hexane:ether (1:1, 50 ml) overnight. The solid was filtered and dried to give the title compound as a solid (3.2-8 g).

Further product was obtained by concentration of the filtrate in vacuo. The resultant orange solid residue was purified by FCC eluting with System A (300:8:1) to give the title compound as a yellow solid (3.38 g).m.p. 120°-121.5° C.

Intermediate 45

3-Chloro-4-hydroxy-N-[4-methoxy-3-(4-methyl-1-piperazinyl) phenyl]benzamide

A mixture of 3-chloro-4-hydroxybenzoic acid (300 mg) and thionyl chloride (2 ml) was treated with DMF (1 drop) and refluxed for lb. Thionyl chloride was evaporated in vacuo and the residue, suspended in THF (2 ml), was added in one portion to a mixture of Intermediate 5 (385 mg) in THF (2 ml) and aqueous sodium hydroxide (2N; 4 ml-). The mixture was stirred for 1 h, diluted with water (25 ml) and washed with dichloromethane (2×100 ml). The aqueous phase was neutralised with hydrochloric acid (2N) and extracted with dichloromethane (3×75 ml). The dried extract was evaporated and the residue was purified by FCC eluting with System B (240:10:1) followed by (190: 10: 1 ) to give the title compound as an orange foam (140 mg). T.l.c. System B (90:10:1) Rf 0.4.

Example 1

N-[4-Methoxy-3-(4-methyl-1-piperazinyl) phenyl]-2'-methyl-4'-(5-methyl -1,2,4-oxadiazol-3-yl) [1,1'-biphenyl]-4-carboxamide A mixture of Intermediate 1 (200 mg) and Intermediate 7 (291 mg) in 1:1 aqueous DME (20 ml) containing sodium carbonate (276 mg) and tetrakis(triphenylphosphine)palladium (0) (18 mg) was heated to reflux for 18 h under nitrogen. The mixture was allowed to cool and silica gel (5 g) added. the solvents were then evaporated and the residue chromatographed on silica gel eluting with System A (200:8:1) to give the title compound as a cream-coloured foam (224 mg).

T.l.c. System A (100:8:1) Rf 0.58.

Assay Found: C,68.25; H,6,1; N,13.35;

$C_{29}H_{31}N_5O_3.058H_2O$ requires C,68.5%; H,6.4; N.13.75%.

Water Determination 2.06% w/w≡0.58 mol % H₂O

Similarly prepared were:

Example 2

N-[4-Methoxy-3-(4-methyl-1-piperazinyl)phenyl]-2'-methyl-4'-(3-methyl-1,2,4-oxadiazol-5-yl)[1,1'-biphenyl]-4-carboxamide as a pale yellow foam (153 mg).

T.l.c. System A (150:8:1) Rf 0.26
Assay Found: C,68.4; H,6.05; N,13.65;
$C_{29}H_{31}N_5O_3.0.45H_2O$ requires C,68.85; H,6.35; N,13.85%.

Water Determination 1.59%w/w≡0.45 %1 mol % $H_2O$

From a mixture of Intermediate 2 (200 mg) and Intermediate 7 (291 mg) in 1:1 aqueous DME (20 ml) containing sodium carbonate (276 mg) and tetrakis(triphenylphosphine)palladium (0) (18 mg).

Example 3

N-[4-Methoxy-3-(4-methyl-1-piperazinyl)phenyl]-2'-methyl-4'-(5-methyl-1,3,4-oxadiazol-2-yl)[1,1'-biphenyl]-4-carboxamide as a colourless foam (136 mg).

T.l.c. System A (100:8:1) Rf 0.44 n.m.r. (CDCl$_3$) δ 2.38 & 2.35 (6H, 2 x s), 2.65 (7H, m+s), 3.15 (4H,m), 3.89 (3H,s), 6.88 (1H,d), 7.25 (1H,m), 7.30 (1H,dd), 7.36 (1H,d), 7.46 (2H, 1/2 AA'BB'), 7.8 (1H, br.s), 7.88–8.01 (4H,m).

From a mixture of Intermediate 10 (149 mg) and Intermediate 7 (218 mg) in 1:1 aqueous DME (20 ml) containing sodium carbonate (206 mg) and tetrakis(triphenylphosphine)palladium (0) (14 mg).

Example 4

N-[4-Methoxy-3-(4-methyl-1-piperazinyl)phenyl]-2'-methyl-5'-methyl 1,3,4-oxadiazol-2-yl)[1,1'-biphenyl]-4-carboxamide as an off-white foam (259 mg)

T.l.c. System A (100:8:1) Rf 0.40
Assay Found: C,67.55; H,6.35; N,13.2;
$C_{29}H_{31}N_5O_3.0.3H_2O.0.4C_2H_6O.0.1CH_2Cl_2$ requires C,67.75; H,6.5; N,13.2%.

Water Determination 1.08%w/w≡0.3 mol $H_2O$.

From a mixture of Intermediate 11 (200 mg) and Intermediate 7 (291 mg) in 1:1 aqueous DME (20 ml) containing sodium carbonate (276 mg) and tetrakis(triphenylphosphine)palladium (0) (18 mg).

Example 5

[4'-[5-(Methoxymethyl)-1,2,4-oxadiazol-3-yl]-N-[4-methoxy-3-(4-methyl-1-piperazinyl)phenyl]-2'-methyl[1,1'-biphenyl]-4-carboxamide as a colourless foam (200 mg).

T.i.c. System A (100:8:1) Rf 0.42
Assay Found: C,67.2; H,6.05; N,12.7;
$C_{30}H_{33}N_5O_4.0.35H_2O$ requires: C,67.5; H,6.35; N,13.1%.

Water Determination 1.16% w/w≡0.35 mol % $H_2O$.

From a mixture of Intermediate 12 (200 mg) and Intermediate 7 (261 mg) in 1:1 aqueous DME (20 ml) containing sodium carbonate (247 mg) and tetrakis(triphenylphosphine)palladium (0) (16 mg).

Example 6

N-[4-Methoxy-3-(4-methyl-1-piperazinyl)phenyl]-2'-methyl-4'-(5-methyl 1,2,4-oxadiazol-3-yl)[1,1'-biphenyl]-4-carboxamide as a colourless foam (100 mg).

T.l.c. System A (100:8:1) Rf 0.40
Assay Found: C,68.75; H,6.25; N,13.3;
$C_{29}H_{31}N_5O_3.0.5H_2O$ requires C,68.75; H,6.35; N,13.8%. From a mixture of 3-(4-bromophenyl)-5-methyl-1,2,4-oxadiazole (100 mg) and Intermediate 14 (160 mg) in 1:1 aqueous DME (20 ml) containing sodium carbonate (146 mg) and tetrakis(triphenylphosphine)palladium (0) (10 mg).

Example 7

N-[4-Chloro-3-(4-methyl-1-piperazinyl)phenyl]-2'-methyl-4'-(5-methyl-1,2,4-oxadiazol-3-yl)[1,1'-biphenyl]-4-carboxamide as a brown foam (122 mg).

T.i.c. System A (100:8:1), Rf 0.56
Assay Found: C,64.9; H,5.65; N,12.9;
$C_{28}H_{28}ClN_5O_2.0.5H_2O.0.4C_2H_6O$ requires C,65.3; H,6.0; N,13.2%.

From a mixture of Intermediate 1 (131 mg) and Intermediate 17 (194 mg) in 1:1 aqueous DME (20 ml) containing sodium carbonate (181 mg) and tetrakis(triphenylphosphine)palladium (0) (12 mg).

Example 8

N-[4-Methoxy-3-(4-methyl-1-piperazinyl) phenyl]-2'-methyl-4'-(3-methyl -1,2,4-thiadiazol-5-yl) [1,1'-biphenyl]-4-carboxamide as a pale yellow foam (65 mg)

T.l.c. System A (100:8:1), Rf 0.42
Assay Found: C,66.15; H,6.0; N,12.8;
$C_{29}H_{31}N_5O_2S.0.75H_2O$ requires C,66.05; H,6.2; N,13.3%.

From a mixture of Intermediate 18 (142 mg) and Intermediate 7 (300 mg) in 1:1 aqueous DME (20 ml) containing sodium carbonate (185 mg) and tetrakis(triphenylphosphine)palladium (0) (12 mg).

Example 9

4'-[3-(Dimethylamino)-1,2,4-oxadiazol-5-yl]-N-[4-methoxy-3-(4-methyl-1-piperazinyl)phenyl]-2'-methyl[1,1'-biphenyl]-4-carboxamide as a cream foam (54 mg)

T.l.c. System A (100:8:1) Rf 0.45
Assay Found: C, 66.65; H, 6.5; N, 14.95;
$C_{30}H_{34}N_6O_3$ $H_2O$ requires: C, 66.15; H, 6.65; N, 15.45%.

From a mixture of Intermediate 19 (50 mg) and Intermediate 7 (103 mg) in 1:1 aqueous DME (10 ml) containing sodium carbonate (63 mg) and tetrakis(triphenylphosphine)palladium (0) (4 mg).

Example 10

N-[4-Methoxy-3-(4-methyl-1-piperazinyl)phenyl]-4'-(5-methyl-1,2,4-oxadiazol-3-yl)[1,1'-biphenyl]-4-carboxamide A mixture of Intermediate 7 (0.75 g), 3-(4-bromophenyl)-5-methyl-1,2,4-oxadiazole (0.49 g), tetrakis(triphenylphosphine)palladium (0) (50 mg) and 2N sodium carbonate (10 ml) in DME (10 ml) was heated under reflux for 3 hours. On cooling, the solution was diluted with 2N sodium carbonate (20 ml), extracted with ethyl acetate (3×50 ml) and the combined extracts dried. The mixture was filtered and the filtrate evaporated to dryness in vacuo. The residue was purified by flash column chromatography on silica eluting with System A (100:8:1) to yield the title compound (0.49 g) as a white solid. m.p. 135°–137° C.

T.l.c. System A (100:8:1) Rf 0.52.

Example 11

2'-Chloro-N-[4-methoxy-3-.(4-methyl-1-piperazinyl)-phenyl]-4'-(5-methyl -1,3,4-oxadiazol-2-yl)[1,1'-biphenyl]-4-carboxamide A mixture of Intermediate 7 (300 mg), Intermediate 21 (557 mg), and sodium carbonate (86 mg) in water (5 ml) and DME (filtered through alumina, 5 ml), was deoxygenated for 5 min with nitrogen. Tetrakis(triphenylphosphine)palladium (0) (19 mg) was then added and the reaction heated at reflux, with stirring under nitrogen for 17 h. The reaction mixture was diluted with water (10 ml) and then extracted with dichloromethane (3×15 ml). The combined extracts were dried and evaporated in vacuo to give a brown solid. Purification by column chromatography on silica and eluting with System A (200:8:1) gave a pale yellow solid (130 mg). This solid was taken up in dichloromethane and ethanol and then filtered, evaporated in vacuo to give the title compound as a yellow solid (91 mg), m.p. 225°–229° C.

T.l.c. System A (50:8:1), Rf=0.74

Example 12

N-[4-Methoxy-3-(4-methyl-1-piperazinyl)phenyl]-4'-(1-methyl-1H -1,2,3-triazol-4-yl)[1,1'-biphenyl]-4-carboxamide A mixture of Intermediate 7 (334 mg), 4-(4-bromophenyl)-1-methyl-1H -1,2,3-triazole (140 mg), tetrakis(-triphenylphosphine)palladium (0) (20 mg), aqueous sodium carbonate (2N, 2 ml), and DME (8 ml) was refluxed under nitrogen for 5 h. The mixture was treated with water (50 ml) and extracted with dichloromethane (3×50 ml). The dried extract was evaporated to give a brown solid which was triturated with ether:dichloromethane (2:1; 30 ml) and purified by FCC eluting with System B (240:10:1) followed by (190:10:1) to give the title compound as a pale yellow solid (95 mg)

T.l.c. System B (90:10:1) Rf 0.4.

n.m.r. (D$_4$CH$_3$OD) δ 2.37 (3H,s), 2.66(4H,br.m), 3.12 (4H, br.m), 3.86

(3H,s), 4.18(3H,s), 6.97 (aH,d), 7.33–7.43 (2H,m), 7.44–7.88 (4H, 2x 1/2AA'BB'), 7.95 (2H, 1/2AA'BB'), 8.03 (2H, 1/2 AA'BB'), 8.34 (1H,s).

Example 13

N-[4-Methoxy-3-(4-methyl-1-piperazinyl)phenyl]-2'-methyl-4'-1,2,3-thiadiazol -4-yl)[1,1'-biphenyl]-4-carboxamide A mixture of Intermediate 22 (121 mg), Intermediate 7 (270 mg), palladium acetate (5 mg) and tri-(orthotolyl)phosphine (15 mg) were dissolved in DMF (2 ml) and TEA (1 ml) and was heated to 100° C. under nitrogen for 18 h. The mixture was allowed to cool, and was partitioned between water (50 ml) and ethyl acetate (2×30 ml). The dried extracts were evaporated to give a bright yellow oil. This material was chromatographed on silica gel eluting with System A (200:8:1) to give the title compound as a yellow foam (86 mg)

T.l.c. System A (100:8:1) Rf 0.40

Assay Found: C, 66.55; H, 5.95; N, 12.5;

C$_{28}$H$_{29}$N$_5$O$_2$S 0.5H$_2$O requires; C, 66.1; H, 5.95; N, 13.75%.

Example 14

2'-Methyl-N-[4-methyl-3-(4-methyl-1-piperazinyl)-phenyl]-4'-(5-methyl -1,3,4-oxadiazol-2-yl)[1,1'-biphenyl]-4-carboxamide A solution of Intermediate 26 (962 mg) in dry THF (15 ml) was cooled to −75° C. and treated dropwise with n-butyllithium (5.6 ml of 1.56 molar solution in hexane) under nitrogen. The resulting solution was stirred for 1.5 hours at −75° C. and was then treated dropwise with triisopropylborate (2.0 ml, 1.63 g). The reaction mixture was then allowed to warm to room temperature before treating with water (3 ml) and evaporating in vacuo to remove excess organic solvent. The aqueous residue, containing a cream coloured gum was washed thoroughly with ethyl acetate before neutralising with 2N hydrochloric acid. On scratching the gum, solidification occurred. The suspension was left to stand for 72 hours and the solid which separate was filtered and washed with water (2×2 ml). The solid was dried in vacuo at 60° C. to give a boronic acid intermediate as a white solid (245 mg) which was used without purification. A solution of this (240 mg) in DME (8 ml) containing a sodium carbonate (2N, 2 ml) and tetrakis(triphenylphosphine)palladium (0) (20 mg) under nitrogen, was treated with Intermediate 10 (150 mg). The mixture was heated at reflux for 18 hours before cooling to room temperature, adding to water (50 ml) and extracting the mixture with dichloromethane (2×50 ml), and then ethyl acetate (50 ml). The combined, dried extracts were concentrated in vacuo and the residue purified by flash column chromatography .luring with a gradient of System A (450:8:1 to 300:8:1) gave the title compound as a white foam (195 mg)

Assay Found: C,70.7; H, 6.5; N,13.8;

C$_{29}$H$_{31}$H$_5$O$_2$.0.5H$_2$O requires: C,71.0; H, 6.5; N,14.3%.

n.m.r (CDCl$_3$) δ 2.28 (3H,s), 2.36 (6H, 2xs), 2.60 (4H,m), 2.64

(3H,s), 3.0(4H,m), 7.18 (1H,d), 7.25–7.4 (3H,m), 7.46 (2H,d), 7.81(1H,s), 7.91 (1H,dd), 8.0 (1H,s).

Example 15

4'-(3-Amino-1,2,4-oxadiazol-5-yl)-N-[4-methoxy-3-(4-methyl-1-piperazinyl) phenyl]-2'-methyl-[1,1'-biphenyl]-4-carboxamide Sodium (0.24 g) was dissolved in absolute ethanol (10 ml) under nitrogen and hydroxyguanidine sulphate (2:1) (salt) (0.95 g) added. The mixture was stirred for 40 minutes and Intermediate 27 (1 g) added. The mixture was heated under reflux for 20 hours and after cooling, the solvent was evaporated in vacuo. The residue was purified by FCC eluting with System A (100: 8: 1 ) and the eluate evaporated to dryness to give the title compound (22 mg) as a pale yellow solid. m.p. 169°–171°.

T.l.c. System A (100:8:1) Rf 0.26.

Example 16

N-[4-Methoxy-3-(4-methyl-1-piperazinyl)phenyl]-2'-methyl-4'-[[5-(methylsulphonyl)methyl]-1,2,4-oxadiazol-3-yl][1,1'-biphenyl]-4-carboxamide A mixture of Intermediate 29 (123 mg) and Intermediate 7 (189 mg) in TEA (1 ml) and DMF (2 ml) containing palladium acetate (5 mg) and tri-o-tolylphosphine (15 mg) was treated according to the method of Example 13, to give the title compound as a buff powder (68 mg) m.p. 146°–148°

T.l.c. System A (100:8:1) Rf 0.41

Example 17

N-[4-Methoxy-3-(4-methyl-1-piperazinyl)phenyl]-2'-methyl-4'-(5-methyl-1,3,4-thiadiazol-2-yl)[1,1'-biphenyl]-4-carboxamide A mixture of Intermediate 31 (150 mg), Intermediate 7 (ca. 30% pure 754 mg) and tetrakis(triphenylphosphine)palladium (0) (20 mg) in 1:1 aqueous DME (20 ml) was treated according to the method of Example 1 to give the title compound as a pale yellow foam (183 mg).

T.l.c. System A (100:8:1) Rf 0.38

Assay Found: C, 64.95; H, 6 15; N, 12.5;
$C_{29}H_{31}N_5O_2S.0.8C_2H_6O$ $0.75H_2O$ requires: C, 65.15; H, 6.65; N, 12.4%.

Example 18

4'-[5-(Hydroxymethyl)-1,2,4-oxadiazol-3-yl]-N-[4-methoxy-3-(4-methyl-1-piperazinyl)phenyl]-2'-methyl[1,1'-biphenyl]-4-carboxamide A mixture of Intermediate 7 (258 mg), Intermediate 32 (130 mg) and tetrakis(triphenylphosphine)palladium (0) (10 mg) in 1:1 aqueous DME (20 ml) was treated according to the method of Example 1 to give the title compound (205 mg) as a colourless powder m.p. 175°–178°.

T.l.c. System A (100:8:1) Rf 0.12.

Example 19

4'-(1,5-Dimethyl-1H-1,2,4-triazol-3-yl)-N-[4-methoxy-3-(4-methyl-1-piperazinyl)phenyl]-2'-methyl[1,1'-biphenyl]-4-carboxamide A mixture of Intermediate 34 (144 mg) and Intermediate 7 (200 mg) was heated to reflux in 1:1 aqueous DME (20 ml) in the presence of sodium carbonate (189 mg) and tetrakis(triphenylphosphine)palladium (0) (12 mg) was treated according to the method of Example 1 to give the title compound as a cream-coloured foam (83 mg).

T.l.c. System A (100:8:1) Rf 0.20

Assay Found: C,68.1; H,6.6; N,15.35;
$C_{30}H_{34}N_6O_2.0.3CH_2Cl_2$ requires C,67.9; H,6.5; N,15.65%.

Example 20

N-[4-Hydroxy-3-(4-methyl-1-piperazinyl)phenyl]-2'-methyl-4'-(5-methyl-1,2,4-oxadiazol-3-yl)[1,1'-biphenyl]-4-carboxamide A mixture of the product of Example 1 (91 mg) and pyridine hydrochloride (2 g) was heated to 180°–190° for 8 h. Sodium bicarbonate (8%; 30 ml) was added and the mixture extracted with dichloromethane (2×25 ml). The dried extracts were evaporated to give a dark oil. This material was chromatographed on silica gel (Merck 7729, 10 g) eluting with System A (200:8:1) to give the title compound as a colourless foam (27 mg).

T.l.c. System A (100:8:1) Rf 0.40.

Assay Found: C,68.15; H,6.0; N,13.8;
$C_{28}H_{29}N_5O_3.0.5H_2O$ requires C,68.25; H,6.15; N,14.2%.

Example 21

N-[4-Methoxy-3-(4-methyl-1-piperazinyl)phenyl]-2-methyl-4'-(5-methyl-1,2,4-1H-triazol-3-yl)[1,1'-biphenyl]-4-carboxamide Intermediate 27 (300 mg) was dissolved in methanol (10 ml), heated to reflux for 2 days with hydrazine hydrate (0.44 ml) and the mixture cooled and poured into water (75 ml). The solid precipitate was collected by filtration and dried. The solid was dissolved in ethanol (5 ml) and was heated to reflux in the presence of ethyl acetimidate hydrochloride (156 mg) and TEA (0.17 ml) for 18 h. The mixture was then evaporated to dryness and the residue purified by FCC eluting with System A (100:8:1) to give the title compound as a colourless foam (83 mg).

T.l.c. System A (50:8:1) Rf 0.63

Assay Found: C, 66.75; H, 6.7; N, 15.65;
$C_{29}H_{32}N_6O_2.0.4C_2H_6O. H_2O$ requires C, 67.15; H, 6.65; N, 15.75%.

Example 22

2-Chloro-N-[4 -methoxy-3-(4-methyl-1-piperazinyl) phenyl]-4'-(5-methyl-1,2,4-oxadiazol-3-yl) [1,1'-biphenyl]-4-carboxamide Trifluoromethanesulphonic anhydride (110 mg) was added dropwise to a solution of Intermediate 45 (130 mg) and pyridine (50 mg) in dichloromethane (2 ml). The solution was stirred for 1 hand evaporated. The residue was treated with Intermediate 40 (102 mg), potassium phosphate (tribasic) (212 mg), dioxan (3 ml) and bis(diphenylphosphinoferrocenyl) palladium (II) chloride (5 mg) and was heated at reflux under nitrogen for 16 h. The cooled mixture was added to aqueous sodium carbonate (2N; 10 ml) and extracted with dichloromethane (3×20 ml). The dried extract was evaporated and the residue was purified by FCC eluting with System B (190:10:1) to give a yellow gum. The gum was treated with ether (5 ml) and evaporated to give the title compound as a yellow solid (35 mg) m.p. 93°–95°

T.l.c. System B (90:10:1) Rf 0.5.

Example 23

N-[2-Fluoro-4-methoxy-5-(4-methyl-1-piperazinyl)-phenyl]-2-methyl-4'-(5-methyl-1,2,4-oxadiazol-3-yl)[1,1'-biphenyl]-4-carboxamide A mixture of Intermediate 39 (438 mg) and 2M sodium carbonate (1 ml) in DME (4 ml) was treated with tetrakis(triphenylphosphine)palladium (0) (20 mg). After stirring under nitrogen for 5 minutes, Intermediate 40 (186 mg) was added. The mixture was heated to reflux and stirred for 24 hours. Additional catalyst (20 mg), aqueous sodium carbonate (0.5 ml) and Intermediate 40 (45 mg) was added and the mixture heated to reflux again for 8 hours. The mixture was cooled to room temperature and poured into 1N sodium carbonate (50 ml). The aqueous layer was extracted with dichloromethane (2×50 ml) and the combined, dried extracts were concentrated in vacuo to give a brown foam which was purified by FCC eluting with System A (200:8:1) to give a pale pink oil which was crystallised upon cooling. The solid was dried in vacuo at 50° C. for 8 hours to give the title compound as a pale pink crystalline solid (385 mg). m.p. 192°–193° C.

Analysis found C,63.9; H,6.3; N,11.8

$C_{29}H_{30}FN_5O_3.0.8C_2H_6O.1.2H_2O$ Requires: C,64.0; H,6.5; N,12.2%.

Example 24

N-[4-Chloro-3-(4-methyl-1-piperazinyl)phenyl]-2'-methyl-4'-(5-methyl-1,2,4-oxadiazol-3-yl) [1,1'-biphenyl]-4-carboxamide (Alternative preparation)

To a stirred solution of Intermediate 42 (400 mg) in dry pyridine (10 ml) was added dropwise thionyl chloride (0.11 ml). The mixture was stirred at 20° for 1 h and then a solution of Intermediate 16 (307 mg) in dry pyridine (5 ml) was added. Stirring was maintained for 18 h and then the mixture was partitioned between 8% sodium bicarbonate (50 ml) and ethyl acetate (2×70 ml). The dried extracts were evaporated to give a yellow oil which was purified by FCC eluting with System A (200:8:1) to give the title compound as an off-white foam (500 mg).

T.l.c. System A (100:8:1) Rf 0.56

Assay Found: C, 66.2; H,5.7; N, 13.55;

$C_{28}H_{28}ClN_5O_2$. $0.25H_2O$ requires: C, 66.4; H, 5.65; N, 13.8%.

Example 25

N-[4-Chloro-3-(4-methyl-1-piperazinyl)phenyl]-2'-methyl-4'-(5-methyl-1,3,4-oxadiazol-2-yl) [1,1'-biphenyl]-4-carboxamide To a cold (0°) stirred solution of Intermediate 41 (200 mg) in dry pyridine (5 ml) was added thionyl chloride (0.06 ml). The mixture was stirred for 0.5 h and then Intermediate 16 (153 mg) was added. The mixture was stirred for 1 h at 20° and then at 80° for 18 h. The solvents were then evaporated and the residue purified by FCC eluting with System A (200:8:1) to give the title compound as a yellow foam (128 mg).

T.l.c. System A (100:8:1) Rf 0.38

Assay Found C, 65.6; H, 5.6; N, 13.35;

$C_{28}H_{28}ClN_5O_2$. $0.5H_2O$ requires C, 65.8; H, 5.7; N, 13.7%.

Example 26

N-[4-Bromo-3-(4-methyl-1-piperazinyl)phenyl]-2'methyl-4'-(5-methyl -1,2,4-oxadiazol-3-yl)[1,1'-biphenyl]-4-carboxamide A suspension of Intermediate 42 (300 mg), in dry dichloromethane (3 ml) was cooled to 0° C. and treated with TEA (1 ml of a 1.2M solution in dichloromethane). After a few minutes all material was in solution, and this was treated slowly with ethyl chloroformate (1 ml of a 1.2M solution in dichloromethane). The mixture was stirred at room temperature for 1 hour before treating with a solution of Intermediate 44 (280 mg) in dichloromethane (1 ml). After 12 hours at room temperature the reaction was heated to 40° for 24 hours. The mixture was then cooled to room temperature, added to water (20 ml) and extracted with dichloromethane (3×20 ml). The organic extracts were dried and concentrated in vacuo to give an orange residue which was purified by FCC eluting with System A (200:8:1) to give a yellow solid. This was triturated in ether to give the title compound as a yellow crystalline solid (125 g) m.p. 151°–153° C.

Analysis: Found: C, 61.8; H, 5.3; N, 12.5.

$C_{28}H_{28}BRN_5O_2$ Requires: C, 61.5; H, 5.2; N, 12.8%.

Example 27

N-[4-Methoxy-3-(4-methyl-1-piperazinyl)phenyl]-2'-methyl-4'-(1,3,4-oxadiazol-2-yl)[1,1'-biphenyl]-4-carboxamide Intermediate 27 (300 mg) was dissolved in methanol (10 ml) and was heated to reflux for 2 days with hydrazine hydrate (0.44 ml). The mixture was cooled and poured into water (75 ml). The solid precipitate was collected by filtration (211 mg) and dried. 160 mg of this material was dissolved in 1,1,1-triethoxyethane (10 ml) and was heated to reflux for 3 h. The solvent was then evaporated giving a brown gum. This material was purified by FCC eluting with System A (200:8:1) to give the title compound as a pale yellow gum (43 mg).

T.l.c. System A (100:8:1) Rf 0.38

Assay Found: C,64.75; H,6,25; N,12.5;

$C_{28}H_{29}N_5O_3.0.6C_2H_6O.1.5H_2O$ requires: C,65.1; H,6.65; N,13.0%.

Example 28

N-[4-Methoxy-3-(4-methyl-1-piperazinyl)-2-methyl-4-(5-methyl -1,2,4-oxadiazol-3-yl)[1,1'-biphenyl]-4-carboxamide (a) hydrochloride A suspension of the compound of Example 1 (4.05 g) in isopropanol (73 ml) was heated, under nitrogen, at 70° C. to effect dissolution of the solid. Further isopropanol (8 ml) was added and heating continued at 76° C. to give a bright pale yellow solution. Concentrated hydrochloric acid (0.77 ml) was added and the solution allowed to cool, with stirring, to 40° C. once crystallisation had begun, the solution was cooled, with stirring, for a further 3 hours in an ice-water bath. The solid was filtered, washed with isopropanol (2×12 ml) and dried in vacuo to give the hydrochloride of the title compound (4.37 g) as pale cream-coloured crystals. m.p. 256° C. (approx).

Analysis Found: C,62.1; H,6.3; N,11.9; Cl,5.9;

$C_{29}H_{31}N_5O_3.HCl.1.7H_2O.0.2C_3H_8O$ requires C,62.65; H,6.5; N,12.1; Cl,6.15%.

(b) methanesulphonate

A suspension of the compound of Example 1 (3.98 g) in IMS (60 ml) was heated, under nitrogen, to 70° C. to effect dissolution of the solid. Heating was stopped and a solution of methanesulphonic acid (0.67 ml) in IMS (4 ml) was added at 65° C. The solution was allowed to cool, with stirring, to 35° C. and was then seeded to initiate crystallisation. The solution was stirred for a further 1.5 hours in an ice-water bath. The solid was filtered, washed with IMS (2×12 ml) and dried in vacuo to give the methanesulphonate of the title compound (4.37 g) as a white solid. m.p. 256° C.

Analysis Found: C,59.4; H,6.1; N,11.4; S,5.2;

$C_{29}H_{31}N_5O_3.CH_4O_3S.H_2O$ requires C,58.9; H,6.1; N,11.45; S,5.2%.

(c) sulphate

A suspension of the compound of Example 1 (4.12 g) in IMS (62 ml) was treated with a solution of concentrated sulphuric acid (0.50 ml) in IMS (4 ml) according to the method of Example 28(b), to give the sulphate of the title compound (4.50 g) as a white solid, m.p. 207°–218° C. (decomp).

Analysis Found: C,58.2; N,5.7; N,11.4; S,5.1; $C_{29}H_{31}N_5O_3.0.9H_2SO_4.0.1C_2H_6O_4S$ requires C,58.6; H,5.6; N,11.7; S,5.4%.

(d) phosphate

A suspension of the compound of Example 1 (4.10 g) in IMS (62 ml) was treated with a solution of phosphoric acid (0.62 ml) in IMS (4 ml) according to the method of Example 28(b), to give the phosphate of the title compound (4.41 g) as a white solid. m.p. 206° C.

Analysis Found: C,57.3; H,5.8; N,11.4; P,5.3; $C_{29}H_{31}N_5O_3.H_3O_4P.0.75H_2O$ requires C,57.2; H,5.9; N,11.5; P,5.1%.

The following examples illustrate pharmaceutical formulations according to the invention. The term "active ingredient" is used herein to represent a compound of formula (I).

Pharmaceutical Example 1

| Oral Tablet A | |
| --- | --- |
| Active Ingredient | 700 mg |
| Sodium starch glycollate | 10 mg |
| Microcrystalline cellulose | 50 mg |
| Magnesium stearate | 4 mg |

Sieve the active ingredient and microcrystalline cellulose through a 40 mesh screen and blend in a appropriate blender. Sieve the sodium starch glycollate and magnesium stearate through a 60 mesh screen, add to the powder blend and blend until homogeneous. Compress with appropriate punches in an automatic tablet press. The tablets may be coated with a thin polymer coat applied by the film coating techniques well known to those skilled-in the art. Pigments may be incorporated in the film coat.

Pharmaceutical Example 2

| Oral Tablet B | |
| --- | --- |
| Active Ingredient | 500 mg |
| Lactose | 100 mg |
| Maize Starch | 50 mg |
| Polyvinyl pyrrolidone | 3 mg |
| Sodium starch glycollate | 10 mg |
| Magnesium stearate | 4 mg |
| Tablet Weight | 667 mg |

Sieve the active ingredient, lactose and maize starch through a 40 mesh screen and blend the powders in a suitable blender. Make an aqueous solution of the polyvinyl pyrrolidone (5–10% w/v). Add this solution to the blended powders and mix until granulated; pass the granulate through a 12 mesh screen and dry the granules in a suitable oven or fluid bed dryer. Sieve the remaining components through a 60 mesh screen and blend them with the dried granules. Compress, using appropriate punches, on an automatic tablet press.

The tablets may be coated with a thin polymer coat applied by film coating techniques well known to those skilled in art. Pigments may be incorporated in the film coat.

Pharmaceutical Example 3

| Inhalation Cartridge | |
| --- | --- |
| Active Ingredient | 1 mg |
| Lactose | 24 mg |

Blend active ingredient, particle size reduced to a very fine particle size (weight mean diameter ca. 5 μm) with the lactose in a suitable powder blender and fill the powder blender into No. 3 hard gelatin capsules.

The contents of the cartridges may be administered using a powder inhaler.

Pharmaceutical Example 4

| Injection Formulation | |
| --- | --- |
| | % w/v |
| Active ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of formula (I):

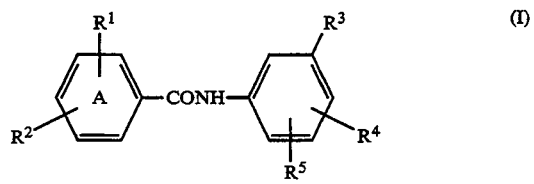

or a physiologically acceptable salt or solvate thereof wherein $R^1$ represents a hydrogen atom or a halogen atom or a group selected from $C_{1-6}$alkyl and $C_{1-6}$alkoxy;

$R^2$ represents a phenyl group substituted by a group selected from

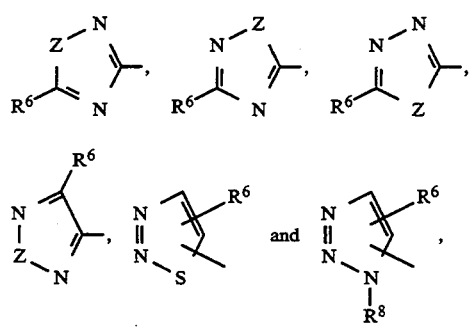

said phenyl group being optionally further substituted by one or two substituents selected from halogen atoms, $C_{1-6}$alkoxy, hydroxy and $C_{1-6}$alkyl; $R^3$ represents the group

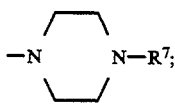

$R^4$ and $R^5$ which may be the same or different each independently represent a hydrogen atom or a halogen atom or a group selected from hydroxy, $C_{1-6}$alkoxy and $C_{1-6}$alkyl;

$R^6$ represents a hydrogen atom or a group selected from $-NR^9R^{10}$ and a $C_{1-6}$alkyl group optionally substituted by one or two substituents selected from $C_{1-6}$alkoxy, hydroxy, $C_{1-6}$acyloxy or $-SO_2R^{11}$;

$R^7$, $R^8$ and $R^9$, which may be the same or different, each independently represent a hydrogen atom or a $C_{1-6}$alkyl group;

$R^{10}$ represents a hydrogen atom or a group selected from $C_{1-6}$alkyl, $C_{1-6}$acyl benzoyl and $-SO_2R^{11}$;

$R^{11}$ represents a $C_{1-6}$alkyl group or a phenyl group;

Z represents an oxygen atom or a group selected from $NR^8$ and $S(O)_k$; and k represents zero, 1 or 2.

2. A compound of formula (I):

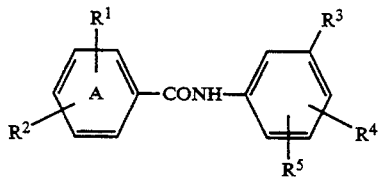

or a physiologically acceptable salt or solvate thereof wherein $R^1$ represents a hydrogen atom or a halogen atom or a group selected from $C_{1-6}$alkyl and $C_{1-6}$alkoxy;

$R^2$ represents a phenyl group substituted by a group selected from

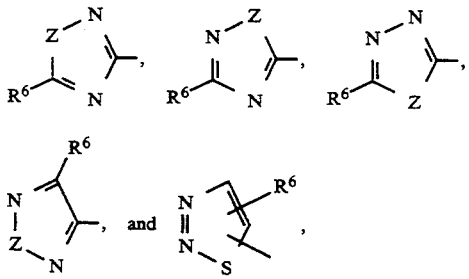

said phenyl group being optionally further substituted by one or two substituents selected from halogen atoms, $C_{1-6}$alkoxy, hydroxy and $C_{1-6}$alkyl; $R^3$ represents the group

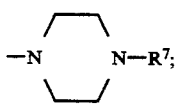

$R^4$ and $R^5$, which may be the same or different, each independently represent a hydrogen atom or a halogen atom or a group selected from hydroxy, $C_{1-6}$alkoxy and $C_{1-6}$alkyl;

$R^6$ represents a hydrogen atom or a group selected from $-NR^9R^{10}$ and a $C_{1-6}$alkyl group optionally substituted by one or two substituents selected from $C_{1-6}$alkoxy, hydroxy and $C_{1-6}$acyloxy;

$R^7$, $R^8$ and $R^9$, which may be the same or different, each independently represent a hydrogen atom or a $C_{1-6}$alkyl group;

$R^{10}$ represents a hydrogen atom or a group selected from $C_{1-6}$alkyl, $C_{1-6}$acyl, benzoyl and $-SO R^{11}$;

$R^{11}$ represents a $C_{1-6}$alkyl group or a phenyl group;

Z represents an oxygen atom or a group selected from $NR^8$ and $S(O)_k$; and k represents zero, 1 or 2.

3. A compound according to claim 1 wherein the substituent of formula

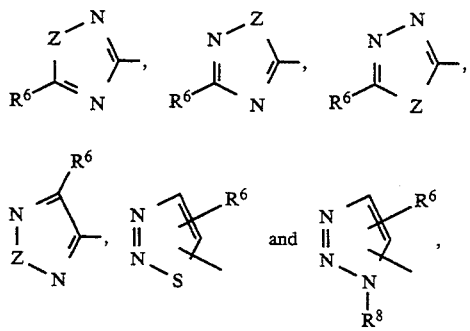

on the phenyl group of $R^2$ is attached at a position meta or para to the bond to the phenyl ring A in general formula (I).

4. A compound according to claim 3 wherein the substituent selected from the group containing

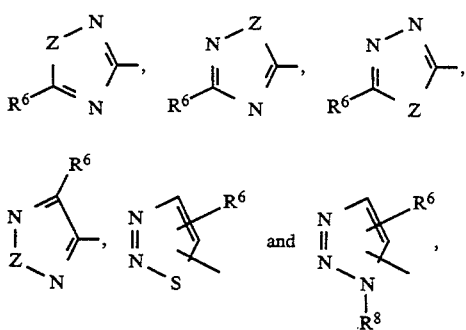

on the phenyl ring of $R^2$ is attached at the position para to the bond to the phenyl ring A in general formula (I).

5. A compound according to claim 1 wherein the phenyl group represented by $R^2$ is additionally substituted by one or two substituents selected from halogen atoms, $C_{1-6}$alkoxy, hydroxy and $C_{1-6}$alkyl, said substituent or substituents being attached at a position ortho to the bond to the phenyl ring A in general formula (I).

6. A compound according to claim 1 wherein $R^2$ represents a phenyl group substituted by the substituent

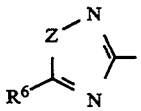

said phenyl group being optionally further substituted by one or two substituents selected from halogen atoms, $C_{1-6}$alkoxy, hydroxy and $C_{1-6}$alkyl.

7. A compound according to claim 1 wherein $R^1$ represents a hydrogen atom or a $C_{1-6}$alkyl group.

8. A compound according to claim 1 wherein $R^1$ represents a methyl group.

9. A compound according to claim 1 wherein Z represents an oxygen atom.

10. A compound according to claim 1 wherein $R^6$ represents a $C_{1-6}$alkyl group optionally substituted by a $C_{1-6}$alkoxy group.

11. A compound according to claim 10 wherein $R^6$ represents a methyl group optionally substituted by a $C_{1-6}$ alkoxy group.

12. A compound according to claim 11 wherein $R^6$ represents a methyl group optionally substituted by a methoxy group.

13. A compound according to claim 1 wherein $R^4$ is attached at the para-position relative to the amide linkage.

14. A compound according to claim 1 wherein $R^4$ represents a halogen atom or a hydroxy or $C_{1-6}$alkoxy group.

15. A compound according to claim 14 wherein $R^4$ represents a fluorine or chlorine atom or a hydroxy or methoxy group.

16. A compound according to claim 1 wherein $R^5$ is a hydrogen atom.

17. A compound according to claim 1 wherein $R^7$ is a $C_{1-3}$alkyl group.

18. A compound according to claim 17 wherein $R^7$ represents a methyl group.

19. A compound of formula (I)

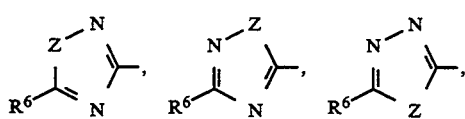

(I)

or a physiologically acceptable salt or solvate thereof wherein $R^1$ represents a hydrogen atom or a halogen atom or a $C_{1-6}$alkyl group;

$R^2$ represents a phenyl group substituted by a group selected from

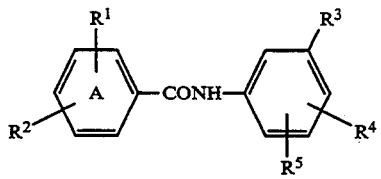

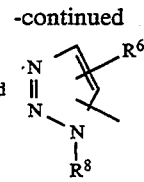

said phenyl group being optionally further substituted by one or two substituents selected from halogen atoms and $C_{1-6}$alkyl;

$R^3$ represents the group

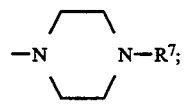

$R^4$ and $R^5$, which may be the same or different each independently represent a hydrogen atom or a halogen atom or a group selected from hydroxy, $C_{1-6}$alkoxy and $C_{1-6}$alkyl;

$R^6$ represents a hydrogen atom or a group selected from $-NR^9R^{10}$ and a $C_{1-6}$alkyl group optionally substituted by one or two substituents selected from $C_{1-6}$alkoxy, hydroxy and $-SO R^{11}$;

$R^7$, $R^8$ and $R^9$ which may be the same or different, each independently represent a hydrogen atom or a $C_{1-6}$alkyl group;

$R^{10}$ represents a hydrogen atom or a $C_{1-6}$alkyl group;

$R^{11}$ represents a $C_{1-6}$alkyl group; and

Z represents a group selected from $-O-$, $NR^8$ and $-S-$.

20. The compound:
N-[4-methoxy-3-(4-methyl-1-piperazinyl)phenyl]-2'-methyl-4'-(5-methyl-1,2,4-oxadiazol-3-yl)[1,1'-biphenyl]-4-carboxamide, or a physiologically acceptable salts and solvates thereof.

21. A compound selected from:
N-[4-methoxy-3-(4-methyl-1-piperazinyl)phenyl]-2'-methyl-4'-(3-methyl-1,2,4-oxadiazol-5-yl) . [1,1'-biphenyl]-4-carboxamide;

N-[4-methoxy-3-(4-methyl-1 -piperazinyl)phenyl]-2'-methyl-4'-(5-methyl-1,3,4-oxadiazol-2-yl) [1,1'-biphenyl]-4-carboxamide;

N-[4-methoxy-3-(4-methyl-1 -piperazinyl)phenyl]-2'-methyl-5'-(5-methyl-1,3,4-oxadiazol-2-yl) [1,1'-biphenyl]-4-carboxamide;

N-[4-methoxy-3-(4-methyl-1-piperazinyl)phenyl]-[4'-[5-(methoxymethyl)-1,2,4-oxadiazol-3-yl]-2'-methyl][1,1'-biphenyl]-4-carboxamide;

N-[4-methoxy-3-(4-methyl-1-piperazinyl)phenyl]-2-methyl-4'-(5-methyl-1,2,4-oxadiazol-3-yl) [1,1'-biphenyl]-4-carboxamide;

4'-[3-(Dimethylamino)-1,2,4-oxadiazol-5-yl]-N-[4-methoxy-3-(4-methyl-1-piperazinyl)phenyl]-2'-methyl[1,1'-biphenyl]-4-carboxamide;

N-[4-Methoxy-3-(4-methyl-1-piperazinyl) phenyl]-4'-(5-methyl-1,2,4-oxadiazol-3-yl) [1,1'-biphenyl]-4-carboxamide;

N-[4-Methoxy-3-(4-methyl-1-piperazinyl) phenyl]-4'-(1-methyl-1H -1,2,3-triazol-4-yl) [1,1'-biphenyl]-4-carboxamide;

N-[4-Methoxy-3-(4-methyl-1-piperazinyl)phenyl]-2'-methyl-4'-[[5-(methylsulphonyl)methyl]-1,2,4-oxadiazol-3-yl][1,1'-biphenyl]-4-carboxamide;

N-[4-Methoxy-3-(4-methyl-1-piperazinyl)phenyl]-2'-methyl-4-(5-methyl-1,3,4-thiadiazol-2-yl)[1,1'-biphenyl]-4-carboxamide;

4'-[5-(Hydroxymethyl)-1,2,4-oxadiazol-3-yl]-N-[4-methoxy-3-(4-methyl-1-piperazinyl)phenyl]-2'-methyl[1,1'-biphenyl]-4-carboxamide;

N-[4-Chloro-3-(4-methyl-1-piperazinyl)phenyl]-2'-methyl-4-(5-methyl-1,2,4-oxadiazol-3-yl)[1,1'-biphenyl]-4-carboxamide;

N-[4-Methoxy-3-(4-methyl-1-piperazinyl)phenyl]-2'-methyl-4'-(3-methyl-1,2,4-thiadiazol-5-yl)[1,1'-biphenyl]-4-carboxamide;

2'-Chloro-N-[4-methoxy-3-(4-methyl-1-piperazinyl)phenyl]-4'-(5-methyl-1,3,4-oxadiazol-2-yl)[1,1',biphenyl]-4-carboxamide;

N-[4-Methoxy-3-(4-methyl-1-piperazinyl)phenyl]-2'-methyl-4-(1,2,3-thiadiazol-4-yl)[1,1'-biphenyl]-4-carboxamide;

2'-Methyl-N-[4-methyl-3-(4-methyl-1-piperazinyl)phenyl]-4'-(5-methyl-1,3,4-oxadiazol-2-yl)[1,1'-biphenyl]-4-carboxamide;

4'-(1,5-Dimethyl-1H-1,2,4-triazol-3-yl)-N-[4-methoxy-3-(4-methyl-1-piperazinyl)phenyl]-2'-methyl[1,1'-biphenyl]-4-carboxamide;

2-Chloro-N-[4-methoxy-3-(4-methyl-1-piperazinyl)phenyl]-4'-(5-methyl-1,2,4-oxadiazol-3-yl)[1,1'-biphenyl]-4-carboxamide;

N-[2-Fluoro-4-methoxy-5-(4-methyl-1-piperazinyl)phenyl]-2-methyl-4'-[5-methyl-1,2,4-oxadiazol-3-yl][1,1'-biphenyl]-4-carboxamide;

N-[4-Chloro-3-(4-methyl-1-piperazinyl)phenyl]-2-methyl-4'-(5-methyl-1,3,4-oxadiazol-2-yl)[1,1'-biphenyl]-4-carboxamide;

N-[4-Bromo-3-(4-methyl-1-piperazinyl)phenyl]-2,methyl-4'-[5-methyl -1,2,4-oxadiazol-3-yl][1,1'-biphenyl]-4-carboxamide;

N-[4-Methoxy-3-(4-methyl-1-piperazinyl]-2'-methyl-4'-(1,3,4-oxadiazol-2-yl)[1,1'-biphenyl]-4-carboxamide;

or a physiologically acceptable salts and solvates thereof.

22. A pharmaceutical composition comprising an effective amount of at least one compound of general formula (I) as defined in claim 1 or a physiologically acceptable salt or solvate thereof, together with at least one physiologically acceptable carrier or excipient.

* * * * *